United States Patent
Turano et al.

(10) Patent No.: US 9,487,792 B2
(45) Date of Patent: Nov. 8, 2016

(54) REGULATORY SEQUENCES TO CONTROL GENE EXPRESSION IN PLANTS

(75) Inventors: Frank J. Turano, Baltimore, MD (US); Kathleen A. Turano, Baltimore, MD (US)

(73) Assignee: Plant Sensory Systems, LLC, Baltimore, MD (US)

( * ) Notice: Subject to any disclaimer, the term of this patent is extended or adjusted under 35 U.S.C. 154(b) by 311 days.

(21) Appl. No.: 14/114,608

(22) PCT Filed: Apr. 23, 2012

(86) PCT No.: PCT/US2012/034661
§ 371 (c)(1),
(2), (4) Date: Oct. 29, 2013

(87) PCT Pub. No.: WO2012/151071
PCT Pub. Date: Nov. 8, 2012

(65) Prior Publication Data
US 2014/0068812 A1    Mar. 6, 2014

Related U.S. Application Data

(60) Provisional application No. 61/482,796, filed on May 5, 2011.

(51) Int. Cl.
*C12N 15/82* (2006.01)

(52) U.S. Cl.
CPC ....... *C12N 15/8216* (2013.01); *C12N 15/8223* (2013.01); *C12N 15/8225* (2013.01)

(58) Field of Classification Search
None
See application file for complete search history.

(56) References Cited

PUBLICATIONS

Potenza et al., In Vitro Cell Dev Biol Plant 40:1-22 (2004).*
Donald & Cashmore, EMBO J 9:1717-26 (1990).*
Kim et al., Plant Mol Biol 24:105-17 (1994).*
Dolferus et al., Plant Physiol 105:1075-87 (1994).*
Saha et al., In Silico Biol 7(1):7-19 (2007).*
Yang et al., GenBank AC189312, 2006.*
Bonke et al., Nature 426:181-84 (2002).*
Oliram & Greb, 20th Int'l Conf Arab Res (2009).*
Sasaki, T. et al., "Oryza Sativa Japonica Group Genomic DNA, Chromosome 2, BAC clone:OSJNBa0073A21," GenBank Accession No. AP005772, Feb. 16, 2008, Nucleotides 108386-106895, 104870-103946, 47 pages.
Kwon, S.J. et al., "Brassica Rapa Subsp. Pekinensis Clone KBrB034L08, Complete Sequence," GenBank Accession No. AC189312, Sep. 11, 2008; Nucleotides 86491-88259, 89853-90511, 30 pages.
International Search Report and Written Opinion, PCT/US2012/34661, Date of mailing: Jul. 18, 2012, 9 pages.

* cited by examiner

*Primary Examiner* — Amjad Abraham
*Assistant Examiner* — Russell Boggs
(74) *Attorney, Agent, or Firm* — Rothwell, Figg, Ernst & Manbeck, p.c.

(57) ABSTRACT

The present invention discloses regulatory sequences, promoters and terminators, and their use in plants. The regulatory sequences can be used to make gene constructs that include a gene not natively associated with the regulatory sequences. Methods to use the regulatory sequences with antisense constructs or functional RNAs are disclosed. Methods to use the regulatory sequences, promoter or terminator, independently of each other are also disclosed. Methods to use the regulatory sequences to improve plant growth and production such as increased biomass, increased yield and increased tolerance to abiotic or biotic stresses are also disclosed.

26 Claims, 2 Drawing Sheets

REGULATORY SEQUENCES TO CONTROL GENE EXPRESSION IN PLANTS

CROSS-REFERENCE TO RELATED APPLICATION

The present application is a national phase entry under 35 U.S.C. §371 of PCT/US2012/034661, filed 23 Apr. 2012, which is related to and claims priority to U.S. provisional patent application Ser. No. 61/482,796 filed 5 May 2011. Each application is incorporated herein by reference in its entirety.

SEQUENCE SUBMISSION

The present application is being filed along with a Sequence Listing in electronic format. The Sequence Listing is entitled 3834110PCTSequenceListing.txt, was created on 16 Apr. 2012 and is 14 kb in size. The information in the electronic format of the Sequence Listing is part of the present application and is incorporated herein by reference in its entirety.

FIELD OF THE INVENTION

The present invention relates to the general technology of plant genetic engineering and, in particular, to the identification of 5' and 3' regulatory sequences, such as promoters and terminators, and their use to improve agricultural performance.

BACKGROUND OF THE INVENTION

The publications and other materials used herein to illuminate the background of the invention, and in particular, cases to provide additional details respecting the practice, are incorporated by reference in their entirety for all that they disclose, and for convenience are referenced in the following text by reference number and are listed by reference number in the appended bibliography.

Recombinant DNA manipulation and genetic engineering can improve crop performance by increasing yield, biomass, and/or tolerance to abiotic or biotic stress. To maximize crop performance the foreign gene needs to be expressed, and the corresponding gene product (RNA or peptide) needs to accumulate, at a specific place and time. Promoters and terminators control developmental, tissue, and temporal gene expression, as well as RNA processing and stability. Together the promoter and terminator can be used to enhance the agronomic, nutritional or pharmaceutical value of a plant or crop.

Promoters

The promoter is usually located upstream (5') of the initiation or start codon (ATG) of the gene (FIG. 1). The in silico identification of putative promoters can be conducted by the recognition of regulatory motifs, such as TATA boxes, TC-motifs, cis-regulatory elements, or core promoter structures (1-4). In addition, putative promoters can also be identified by their physical location to a gene. Genes can be identified by searching genome databases or by scanning databases (5, 6).

In general, the regulatory sequences for an RNA polymerase II-dependent promoter reside in the region approximately 2900 to 35 basepairs (bp) up-stream of the initiation or start codon (ATG) of the gene. For example, the full-length promoter for ACC oxidase from peach is 2919 bp (7), the full-length promoter for cytokinin oxidase from orchid is 2189 bp (8), the full-length promoter for glucuronosyltransferase from cotton is 1647 bp (9), full-length promoter for glutathione peroxidase1 from $Citrus\ sinensis$ is 1600 bp (10), and the full-length promoter for the nodule-enhanced PEP carboxylase from alfalfa is 1277 bp (11). The convention for specifying the position of the nucleotides in a promoter is to identify the number of by prior to the "A" in the start codon. The nucleotide preceding the start codon is designated as −1. The functional regions of a plant promoter are typically between −1700 to −1 bp. However, functional plant promoters can be located between −200 to −1 bp, −500 to −1 bp, −1000 to −1 bp, −1500 to −1 bp, and −2000 to −1 bp.

As mentioned above, the promoter contains the 5' untranslated region (5'UTR) of the transcribed RNA. The 5'UTR may play an important role in the expression of the transcript (12-16) by controlling transcription (17) and RNA stability (18). The 5'UTR (could also control the efficiency of translation (19, 20).

There are many types of promoters. Constitutive promoters provide continuous expression and can vary in strength of expression from weak to strong. They can be used for applications that include, but are not limited to, testing the effects of a gene construct with a selectable marker such as antibiotic, herbicide or chemical resistance or for expression of an antisense construct, RNAi, or a foreign gene. Non-constitutive promoters do not continuously produce transcript or RNA. Non-constitutive promoters may induce or increase transcription of genes in response to a signal, such as an environmental cue or other stress signal including biotic and/or abiotic stresses. Non-constitutive promoters include developmentally preferred promoters, tissue-preferred promoters, tissue-specific promoters, cell-type-specific promoters, and inducible promoters. Developmentally preferred promoters limit expression to specific developmental stages. Tissue-specific or tissue-preferred promoters limit expression to specific cells or tissues that include, but is not limited to, fiber-specific, green tissue-specific, root-specific, stem-specific, flower-specific, vascular-specific, xylem-specific or phloem-specific promoters. Inducible promoters initiate expression in response to stimuli, including, but not limited to, mechanical manipulation, heat, cold, salt, flooding, drought, salt, anoxia, pathogens, such as bacteria, fungi, and viruses, and nutritional deprivation.

Terminators

Terminators are typically located downstream (3') of the gene, after the stop codon (TGA, TAG or TAA). Terminators play an important role in the processing and stability of RNA as well as in translation. Most, but not all terminators, contain a polyadenylation sequence or cleavage site. Examples of specific polyadenylation sequences are AAUAAA or AAUAAU. These sequences are known as the near upstream elements (NUEs) (21). NUEs usually reside approximately 30 bp away from a GU-rich region (22-24), known as far upstream elements (FUEs). The FUEs enhance processing at the polyadenylation sequence or cleavage site, which is usually a CA or UA in a U-rich region (25). Within the terminator, elements exist that increase the stability of the transcribed RNA (26-28) and may also control gene expression (29, 30).

Monocot and Dicot Regulatory Sequences

Some promoters work in both dicotyledonous (dicot) and monocotyledonous (moncot) plants (31), and others, such as chimeric promoters, have been engineered to work in both classes of flowering plants (32). The typical case is that dicotyledonous regulatory sequences control expression in dicots, and monocotyledonous regulatory sequences control expression in monocots. This is particularly true for promoters.

Thus, there is a need in the art to identify and use new regulatory sequences for utilization in plants. The development of plant regulatory sequences for genetic engineering is important to meet the increased demand for the production of food, fiber, feed, biofuel and bio-based materials and nutraceuticals.

SUMMARY OF THE INVENTION

The present invention relates to the identification of regulatory sequences in plants and the methods and compositions for using them to improve agricultural performance. More particularly, the invention relates to the use of polynucleotides that function as promoters or terminators in plants. The transformed plants have the advantage of improved growth and production such as increased biomass, increased yield and increased tolerance to biotic or abiotic stresses.

In one aspect, the present invention provides novel promoters and terminators. In one embodiment, the promoters and terminator are derived from rice (*Oryza sativa*). In another embodiment, a rice promoter has a nucleotide sequence set forth in SEQ ID NO:1, SEQ ID NO:3, SEQ ID NO:4, SEQ ID NO:5, SEQ ID NO:6 or SEQ ID NO:7. In an additional embodiment, a rice terminator has a nucleotide sequence set forth in SEQ ID NO:2. In one embodiment, the promoter and terminator are derived from field mustard (*Brassica rapa*). In another embodiment, a field mustard promoter has a nucleotide sequence set forth in SEQ ID NO:8, SEQ ID NO:10 or SEQ ID NO:11. In an additional embodiment, a field mustard terminator has a nucleotide sequence set forth in SEQ ID NO:9.

In a second aspect, the present invention provides constructs which comprise a promoter operably linked to a DNA of interest which is operably linked to a terminator. In one embodiment, the promoter is a rice promoter of the present invention. In another embodiment, the terminator is the rice terminator of the present invention. In an additional embodiment, the terminator is a terminator known to the skilled artisan. In a further embodiment the terminator is the field mustard terminator of the present invention. In one embodiment, the promoter is a promoter known to the skilled artisan. In another embodiment, the terminator is a rice terminator of the present invention. In an additional embodiment, the terminator is a field mustard terminator of the present invention. In one embodiment, the promoter is a field mustard promoter of the present invention. In another embodiment, the terminator is the field mustard terminator of the present invention. In an additional embodiment, the terminator is a terminator known to the skilled artisan. In a further embodiment the terminator is the rice terminator of the present invention.

In one embodiment, the DNA of interest encodes a polypeptide. In another embodiment, the DNA of interest encodes a functional RNA. In a further embodiment, the DNA of interest encodes antisense RNA or is sense RNA. In one embodiment, the functional RNA is transfer RNA (tRNA). In another embodiment, the functional RNA is ribosomal RNA (rRNA). In an additional embodiment, the functional RNA is small nucleolar RNA (snoRNA). In a further embodiment, the functional RNA is micro RNA (miRNA). In another embodiment, the functional RNA is small inhibitory RNA (siRNA). In another embodiment, the siRNA is a short hairpin RNA (shRNA). In one embodiment, the functional RNA is a double stranded RNA (dsRNA). In another embodiment, the DNA of interest is heterologous to the promoter and/or terminator of the present invention.

In a third aspect, the present invention provides a plant cell transformed with construct of the present invention to provide a transgenic plant cell containing the construct. In one embodiment, the transgenic plant cell is in tissue culture. In another embodiment, the transgenic plant cell is in a transgenic plant. In an additional embodiment, the transgenic plant cell in tissue culture is regenerated into a plant to provide a transgenic plant containing the construct. In one embodiment, the construct is stably incorporated into the transgenic plant cell or the transgenic plant. In another embodiment, the transgenic produce plants produced in accordance with the present invention have advantages of improved and/or modified seed characteristics, such as starch, oil, and the like. In another embodiment, the transgenic produce plants produced in accordance with the present invention have advantages of improved production, such as enhanced plant growth characteristics (root mass, biomass, yield), survival characteristics and/or tolerance to environmental stresses including, but not limited to, drought, salinity, cold or elevated temperature, and/or tolerance to biotic stresses including, but not limited to, insect or nematode feeding, bacterial or fungal infection.

DETAILED DESCRIPTION OF THE INVENTION

Figure 1:
FIG. 1. Schematic representation of a promoter or 5' regulatory region (open box), gene (hatched box), and terminator or 3' regulatory region (gray box).

The present invention describes rice (*Oryza sativa*) and field mustard (*Brassica rapa*) regulatory sequences and their use in plants. The regulatory sequences described in the invention are promoters and terminators that may be used in combination with DNA of interest. The DNA of interest may be a native gene or with foreign genes so that production of the peptide may be regulated as desired. Alternatively, the DNA of interest may encode functional RNA, antisense RNA or sense RNA so that the production of a native protein may be regulated as desired.

Methods of Using the Regulatory Sequences to Improve Crop Quality

The invention can be made using routine recombinant DNA techniques. In some embodiments, regulatory sequences of the present invention are used according to the following general scheme:
  a. operably link a promoter of the invention (SEQ ID NO:1) to the 5' end of a DNA of interest;
  b. operably link a terminator of the invention (SEQ ID NO:2) to the 3' end of the promoter-DNA of interest assembled in step a above;
  c. insert the promoter-DNA of interest-terminator construct assembled in steps a and b above into a vector; and d. transform the vector containing the construct into a plant or plant cell.

Alternatively, in this embodiment the promoter of SEQ ID NO:1 can be replaced by a promoter of SEQ ID NO:3, SEQ ID NO:4, SEQ ID NO:5, SEQ ID NO:6 or SEQ ID NO:7. In one embodiment, the DNA of interest encodes a protein that improves crop quality. In another embodiment, the DNA of interest encodes a functional RNA. In an additional embodiment, the DNA of interest encodes antisense RNA or sense RNA.

In another embodiment, the following general scheme can be used:
a. operably link a promoter of the invention (SEQ ID NO:1) to the 5' end of a DNA of interest;
b. operably link a functional plant terminator to the 3' end of the promoter-DNA of interest assembled in step a above;
c. insert the promoter-DNA of interest-terminator construct assembled in steps a and b above into a vector; and
d. transform the vector containing the construct into a plant or plant cell.

A suitable terminator known to skilled artisan for this embodiment can be, but is not limited to, 3'-regulatory sequences of the CaMV 19S gene (22), nopaline synthase (nos) gene (33), octopine synthase (ocs) gene (34), the potato proteinase inhibitor II gene (35), 1-aminocyclopropane-1-carboxylate synthase 2 (ACS2) gene, alcohol dehydrogenase (ADH) gene, histone H4 (H4) gene, heat shock protein (HSP) gene, ribulose-1,5-bisphosphate carboxylase/oxygenase small subunit (rbcS) gene or ubiquitin 5 (UBQ5) gene (21). In addition, the terminator of SEQ ID NO:9 can be used in this embodiment.

Alternatively, in this embodiment the promoter of SEQ ID NO:1 can be replaced by a promoter of SEQ ID NO:3, SEQ ID NO:4, SEQ ID NO:5, SEQ ID NO:6 or SEQ ID NO:7. In one embodiment, the DNA of interest encodes a protein that improves crop quality. In another embodiment, the DNA of interest encodes a functional RNA. In an additional embodiment, the DNA of interest encodes antisense RNA or sense RNA.

In another, embodiment the following general scheme can be used:
a. operably link a functional plant promoter to the 5' end of a DNA of interest;
b. operably link a terminator of the invention (SEQ ID NO:2) to the 3' end of the promoter-DNA of interest assembled in step a above;
c. insert the promoter-DNA of interest-terminator construct assembled in steps a and b above into a vector; and
d. transform the vector containing the construct into a plant or plant cell.

Suitable promoters known to those of ordinary skill in the art for this embodiment include, but are not limited to, promoters that control expression of genes in green tissue such as the maize from the phosphenol carboxylase gene (31) or root-specific expression (36, 37). Other suitable promoters can be an endogenous, i.e. a promoter native to the species and or cell type being transformed. Alternatively, the promoter can be a foreign promoter, which promotes transcription of a length of DNA of viral, microbes, bacterial or eukaryotic origin, invertebrates, vertebrates including those from plants and plant viruses. For example, in certain preferred embodiments, the promoter may be of viral origin, including a cauliflower mosaic virus promoter (CaMV), such as CaMV 35S or 19S, a figwort mosaic virus promoter (FMV 35S), or the coat protein promoter of tobacco mosaic virus (TMV Promoters of bacterial origin include the acs promoter, the nos promoter and other promoters derived from native Ti plasmids could also be used (38). Other constitutive promoters include, for example, those disclosed in U.S. Pat. Nos. 5,608,149; 5,608,144; 5,604,121; 5,569,597; 5,466,785; 5,399,680; 5,268,463; and 5,608,142. Inducible promoters are described in U.S. Pat. Nos. 6,506,962, 6,575,814, 6,972,349 and 7,301,069 and in U.S. Patent Application Publication Nos. 2007/0061917 and 2007/0143880.

In one embodiment, the DNA of interest encodes a protein that improves crop quality. In another embodiment, the DNA of interest encodes a functional RNA. In an additional embodiment, the DNA of interest encodes antisense RNA or sense RNA.

In a further embodiment, the following general scheme can be used:
a. operably link a promoter of the invention (SEQ ID NO:8) to the 5' end of a DNA of interest;
b. operably link a terminator of the invention (SEQ ID NO:9) to the 3' end of the promoter-DNA of interest assembled in step a above;
c. insert the promoter-DNA of interest-terminator construct assembled in steps a and b above into a vector; and
d. transform the vector containing the construct into a plant or plant cell.

Alternatively, in this embodiment the promoter of SEQ ID NO:8 can be replaced by a promoter of SEQ ID NO:10 or SEQ ID NO:11. In one embodiment, the DNA of interest encodes a protein that improves crop quality. In another embodiment, the DNA of interest encodes a functional RNA. In an additional embodiment, the DNA of interest encodes antisense RNA or sense RNA.

In another embodiment the following general scheme can be used:
a. operably link a promoter of the invention (SEQ ID NO:8) to the 5' end of a DNA of interest;
b. operably link a functional plant terminator to the 3' end of the promoter-DNA of interest assembled in step a above;
c. insert the promoter-DNA of interest-terminator construct assembled in steps a and b above into a vector; and
d. transform the vector containing the construct into a plant or plant cell.

A suitable terminator known to skilled artisan for this embodiment can be, but is not limited to, 3'-regulatory sequences of the CaMV 19S gene (22), nopaline synthase (nos) gene (33), octopine synthase (ocs) gene (34), the potato proteinase inhibitor II gene (35), 1-aminocyclopropane-1-carboxylate synthase 2 (ACS2) gene, alcohol dehydrogenase (ADH) gene, histone H4 (H4) gene, heat shock protein (HSP) gene, ribulose-1,5-bisphosphate carboxylase/oxygenase small subunit (rbcS) gene or ubiquitin 5 (UBQ5) gene (21). In addition, the terminator of SEQ ID NO:2 can be used in this embodiment.

Alternatively, in this embodiment the promoter of SEQ ID NO:8 can be replaced by a promoter of SEQ ID NO:10 or SEQ ID NO:11. In one embodiment, the DNA of interest encodes a protein that improves crop quality. In another embodiment, the DNA of interest encodes a functional RNA. In an additional embodiment, the DNA of interest encodes antisense RNA or sense RNA.

In another embodiment the following general scheme can be used:

a. operably link a functional plant promoter to the 5' end of a DNA of interest;
b. operably link a terminator of the invention (SEQ ID NO:9) to the 3' end of the promoter-DNA of interest assembled in step a above;
c. insert the promoter-DNA of interest-terminator construct assembled in steps a and b above into a vector; and
d. transform the vector containing the construct into a plant or plant cell.

Suitable promoters known to those of ordinary skill in the art for this embodiment include, but are not limited, to promoters that control expression of genes in green tissue such as the maize from the phosphenol carboxylase gene (31) or root-specific expression (36, 37). Other suitable promoters can be an endogenous, i.e. a promoter native to the species and or cell type being transformed. Alternatively, the promoter can be a foreign promoter, which promotes transcription of a length of DNA of viral, microbes, bacterial or eukaryotic origin, invertebrates, vertebrates including those from plants and plant viruses. For example, in certain preferred embodiments, the promoter may be of viral origin, including a cauliflower mosaic virus promoter (CaMV), such as CaMV 35S or 19S, a figwort mosaic virus promoter (FMV 35S), or the coat protein promoter of tobacco mosaic virus (TMV Promoters of bacterial origin include the ocs promoter, the nos promoter and other promoters derived from native Ti plasmids could also be used (38).

In one embodiment, the DNA of interest encodes a protein that improves crop quality. In another embodiment, the DNA of interest encodes a functional RNA. In an additional embodiment, the DNA of interest encodes antisense RNA or sense RNA.

In a further embodiment of the present invention, a vector is made that contains a promoter in accordance with the present invention, such as described in the above embodiments, and a terminator, such as described in the above embodiments, with a cloning site located between the promoter and the terminator. A DNA of interest is inserted into the cloning site to produce a promoter-DNA of interest-terminator construct within the vector. The vector is then transformed into a plant cell or a plant.

Although the above embodiments describe the preparation of a vector which is transformed into a plant cell or a plant, it is also understood that the promoter-DNA of interest-terminator construct can be transformed directly into a plant cell or a plant using transformation techniques described herein.

Suitable Nucleotides for the Promoter and Terminator

The most suitable polynucleotides for the invention include promoters of SEQ ID NO:1, SEQ ID NO:3, SEQ ID NO:4, SEQ ID NO:5, SEQ NO:6, SEQ ID NO:7, SEQ ID NO:8, SEQ ID NO:10 or SEQ ID NO:11 and terminators of SEQ ID NO:2 and SEQ ID NO:9 however, nucleic acid hybridization a technique well known to those of skill in the art of DNA manipulation can be used to identify other suitable polynucleotides. In accordance with the invention other suitable promoters for use may be obtained by the identification of polynucleotides that selectively hybridize to the promoters of SEQ ID NO:1, SEQ ID NO:3, SEQ ID NO:4, SEQ ID NO:5, SEQ ID NO:6, SEQ ID NO:7, SEQ ID NO:8, SEQ ID NO:10 or SEQ ID NO:11 by hybridization under low stringency conditions, moderate stringency conditions, or high stringency conditions. In accordance with the invention other suitable terminators for use may be obtained by the identification of polynucleotides that selectively hybridize to the terminators of SEQ ID NO:2 and SEQ ID NO:9 by hybridization under low stringency conditions, moderate stringency conditions, or high stringency conditions. Selectively hybridizing sequences typically have at least 60% sequence identity, preferably 70-90% sequence identity, and most preferably 91% to 100% sequence identity with each other.

Database searches and homology searches of genome and nucleotide databases identify similar DNA or RNA molecules based on the alignment of nucleotides using algorithms or computer programs and these techniques well known to those of skill in the art. In accordance with the invention other suitable polynucleotides for use may be obtained by the in silico identification of polynucleotides for regulatory sequences with at least 60% sequence identity, preferably 70-90% sequence identity, and most preferably 91% to 100% sequence identity with promoters of SEQ ID NO:1, SEQ ID NO:3, SEQ ID NO:4, SEQ ID NO:5, SEQ ID NO:6, SEQ ID NO:7, SEQ ID NO:8, SEQ ID NO:10 or SEQ ID NO:11 or of terminators of SEQ ID NO:2 and SEQ ID NO:9.

The promoters of the present invention are phloem specific promoters and can control gene expression in phloem tissue. The full length promoters (i.e., SEQ ID NO:1 and SEQ ID NO:8) are phloem specific in phloem tissue throughout the plant. The truncated promoters are phloem specific in phloem tissue within certain regions of the plant.

DNA of Interest

The DNA that is inserted (the DNA of interest) into plant cells or plants is not critical to the transformation process. Generally the DNA that is introduced into a plant is part of a construct. The DNA may be a gene of interest, e.g., a coding sequence for a protein, or it may be a sequence that is capable of regulating expression of a gene, such as a functional RNA, an antisense sequence, a sense suppression sequence, a post-transcriptional gene silencing sequence (an RNAi sequence such as an siRNA, shRNA or dsRNA) or a micro-RNA (miRNA) sequence. In one embodiment, the DNA of interest is heterologous to the promoters and/or terminators of the present invention. In another embodiment, the construct has codon optimization in the DNA of interest and is further modified in the nucleotide sequence around the start codon to optimize expression in transgenic plants (98, 99). The construct typically includes regulatory regions operatively linked to the 5' side of the DNA of interest and/or to the 3' side of the DNA of interest as described herein. A cassette containing all of these elements is also referred to herein as an expression cassette, a nucleic acid construct or an expression construct. The expression cassettes may additionally contain 5' leader sequences in the expression cassette construct. The regulatory regions (i.e., promoters, transcriptional regulatory regions, and translational termination regions) and/or the polynucleotide encoding a signal anchor may be native/analogous to the host cell or to each other. The promoters and tissue-specific promoters identified herein are particularly useful for preparing constructions for the transformation of plants. Alternatively, the regulatory regions and/or the polynucleotide encoding a signal anchor may be heterologous to the host cell or to each other. See, U.S. Pat. No. 7,205,453 and U.S. Patent Application Publication Nos. 2006/0218670, 2006/0248616 and 20090100536, and the references cited therein. The expression cassettes may additionally contain 5' leader sequences in the expression cassette construct. Such leader sequences can act to enhance translation. Translation leaders are known in the art and include those described in International Publication No. WO 2008/094127 and the references cited therein.

The DNA of interest that is under control of a promoter, such as a promoter described herein, may be any DNA as defined herein and may be used to alter any characteristic or trait of a plant species into which it is introduced. In one embodiment, the DNA of interest is introduced into a plant in order to enhance a trait of the plant. In another embodiment, an enhanced agronomic trait may be characterized by enhanced plant morphology, physiology, growth and development, yield, nutritional enhancement, disease or pest resistance, or environmental or chemical tolerance. In some aspects, the enhanced trait is selected from group of enhanced traits consisting of enhanced water use efficiency, enhanced temperature tolerance, increased yield, enhanced nitrogen use efficiency, enhanced seed protein enhanced seed oil and enhanced biomass. Increase yield may include increased yield under non-stress conditions and increased yield under environmental stress conditions. Stress conditions may include, for example, drought, shade, fungal disease, viral disease, bacterial disease, insect infestation, nematode infestation, extreme temperature exposure (cold or hot), osmotic stress, reduced nitrogen nutrient availability, reduced phosphorus nutrient availability and high plant density. In some embodiments, the DNA of interest may be used to modify metabolic pathways, such as fatty acid biosynthesis or lipid biosynthesis pathways in seeds, or to modify resistance to pathogens in plant species. For further description of such DNA of interest, see U.S. Pat. Nos. 5,659,026; 6,437,217; 6,977,325; 7,151,204; and 7,223,569.

In another embodiment, the DNA of interest encodes a metabolic regulator, such as described in U.S. Patent Application Publication No. 2009/0061519 and in copending U.S. patent application Ser. No. 13/095,261 filed 27 Apr. 2011 (U.S. Patent Application Publication No. 2011/0231961), incorporated herein by reference. In an additional embodiment, the DNA of interest encodes an enzyme such as putrescine aminotransferase (PAT) or gamma-aminobutyricaldehyde dehydrogenase (GABAlde DeHase), such as described in U.S. Patent Application Publication No. 2009/0077693 and in copending U.S. patent application Ser. No. 13/095,243 filed 27 Apr. 2011 (U.S. Patent Application Publication No. 2011/0203019), incorporated herein by reference. In a further embodiment, the DNA interest encodes an enzyme such as cysteine dioxygenase (CDO), sulfinoalanine decarboxylase (SAD), glutamate decarboxylase (GAD), taurine-pyruvate aminotransferase, sulfoacetaldehyde acetyltransferase (SA), a small subunit of taurine dehydrogenase (ssTDeHase) or a large subunit of taurine dehydrogenase (lsTDeHase), such as described in International Patent Publication WO 2011/053764.

The DNA of interest can be selected to inhibit expression of a native DNA sequence within a plant's tissues to achieve a desired phenotype. In this case, such inhibition might be accomplished, for example, with transformation of the plant to comprise the promoters described herein linked to an antisense nucleotide sequence, hairpin, RNA interfering or other nucleic acid molecule, such that tissue-preferred expression of the molecule interferes with translation of the mRNA of the native DNA sequence or otherwise inhibits expression of same in a subset of the plant's cells. For further description of RNAi techniques, see, e.g., U.S. Pat. Nos. 5,034,323; 6,326,527; 6,452,067; 6,573,099; 6,753,139; and 6,777,588. See also International Patent Publications WO 97/01952, WO 98/36083, WO 98/53083, WO 99/32619 and WO 01/75164; and U.S. Patent Publications 2003/0175965, 2003/0175783, 2003/0180945, 2004/0214330, 2005/0244858, 2005/0277610, 2007/0265220, 2009/0215860, 2009/0308041 and 2010/0058498.

Where appropriate, the DNA of interest may be optimized for increased expression in the transformed plant. That is, the coding sequences can be synthesized using plant-preferred codons for improved expression. Methods are available in the art for synthesizing plant-preferred genes. See, for example, U.S. Pat. Nos. 5,380,831, 5,436,391, and 7,205,453 and U.S. Patent Application Publication Nos. 2006/0218670 and 2006/0248616.

Cloning Techniques

For purposes of understanding the principles of the invention, reference will now be made to particular embodiments of the invention and specific language will be used to describe the same. The materials, methods and examples are illustrative only and not limiting. Unless mentioned otherwise, the techniques employed or contemplated herein are standard methodologies well known to one of ordinary skill in the art. Specific terms, while employed below and defined at the end of this section, are used in a descriptive sense only and not for purposes of limitation. The practice of the present invention will employ, unless otherwise indicated, conventional techniques of botany, microbiology, tissue culture, molecular biology, chemistry, biochemistry and recombinant DNA technology, which are within the skill of the art[39-46].

A suitable polynucleotide for use in accordance with the invention may be obtained by cloning techniques using genomic libraries, or DNA from rice, *Brassica* or other related species which are available commercially or which may be constructed using standard methods known to persons of ordinary skill in the art. Suitable nucleotide sequences may be isolated from DNA libraries obtained from a wide variety of species by means of nucleic acid hybridization or amplification methods, such as polymerase chain reaction (PCR) procedures, using as probes or primers nucleotide sequences selected in accordance with the invention.

Furthermore, nucleic acid sequences may be constructed or amplified using chemical synthesis (47-49). Chemical synthesis generally produces a single stranded oligonucleotide. This may be converted into double stranded DNA by hybridization with a complementary sequence or by polymerization with a DNA polymerase using the single strand as a template. If the particular nucleic acid sequence is of a length that makes chemical synthesis of the entire length impractical, the sequence may be broken up into smaller segments that may be synthesized and ligated together to form the entire desired sequence by methods known in the art. Gene constructs can be synthesized commercially by several vendors that include, but are not limited to, Bio Basic, Bio-Synthesis, DNA2.0, Epoch Life Science, GENEART, GENEWIZ, GenScript, Hyglos GmbH, Integrated DNA Technologies, Invitrogen, or Primm Biotech.

A suitable polynucleotide for use in accordance with the invention may be constructed by recombinant DNA technology, for example, by cutting or splicing nucleic acids using restriction enzymes and mixing with a cleaved (cut with a restriction enzyme) vector with the cleaved insert (DNA of the invention) and ligated using DNA ligase. Alternatively amplification techniques, such as PCR, can be used, where restriction sites are incorporated in the primers that otherwise match the nucleotide sequences (especially at the 5' ends) selected in accordance with the invention. The desired amplified recombinant molecule is cut or spliced using restriction enzymes and mixed with a cleaved vector and ligated using DNA ligase. In another method, after amplification of the desired recombinant molecule, DNA linker sequences are ligated to the 5' and 3' ends of the desired nucleotide insert with ligase, the DNA insert is cleaved with a restriction enzyme that specifically recognizes sequences present in the linker sequences and the desired vector. The cleaved vector is mixed with the cleaved insert, and the two fragments are ligated using DNA ligase. In yet another method, the desired recombinant molecule is amplified with primers that have recombination sites (e.g. Gateway) incorporated in the primers, that otherwise match the nucleotide sequences selected in accordance with the invention. The desired amplified recombinant molecule is mixed with a vector containing the recombination site and recombinase, the two molecules are fused together by recombination.

The recombinant expression cassette or DNA construct includes a promoter of the invention operably linked to a polynucleotide of a gene, which is operably linked to a terminator of the invention. In various aspects of the invention described herein, a variety of different types of polynucleotides can be used. As used herein, a polynucleotide is "operably linked" to a promoter or terminator when it is placed into a functional relationship with the promoter or terminator. The functional relationship between a promoter or terminator and a desired polynucleotide insert typically involves the polynucleotide and the promoter or terminator sequences being contiguous such that transcription of the polynucleotide sequence will be facilitated. Two nucleic acid sequences are further said to be operably linked if the nature of the linkage between the two sequences does not (1) result in the introduction of a frame-shift mutation; (2) interfere with the ability of the promoter or terminator sequence to direct the transcription of the desired polynucleotide sequence, or (3) interfere with the ability of the desired polynucleotide sequence to be transcribed by the promoter or terminator sequence region. Typically, the promoter element is generally upstream (i.e., at the 5' end), and the terminator element is generally downstream (i.e., at the 3' end) of the polynucleotide sequence.

Bacterial Vectors

A wide variety of vectors may be employed to clone plant DNA into a bacterial cell with a construct made or selected in accordance with the invention, including plasmids (including high and low copy number plasmids), phage vectors (including M13 and lambda) and cosmids. Such vectors, as well as other vectors, are well known in the art. Use of cloning vectors, expression vectors, adapters, and linkers is well known in the art these include but are not limited to vectors as: M13, lambda ZAP, lambda ZAP II, lambda gt10, lambda gt11, pBK-RSV, pBluescript II, lambda DASH II, lambda EMBL 3, lambda EMBL 4, pWE15, SuperCos 1, SurfZap, Uni-ZAP, pBC, pSG5, pBK, pCR-Script, pET, pGEM, pGEX, pSPORTI and pCR4.

Plant Vectors

T-DNA vector systems can be used to transfer foreign DNA into plants (50). The vectors can be chosen such that the regulatory sequences which are operably linked to a gene therein will become incorporated into the genome of the plant. Suitable plant vectors also typically contain a marker gene, which confers a selectable phenotype on plant cells as described herein.

Typical vectors useful for expression of genes in higher plants are well known in the art and include vectors derived from the tumor-inducing (Ti) plasmid of *Agrobacterium tumefaciens* described in Rogers et al. (51). Ti-plasmids are vectors that integrate a portion of vector DNA into the genome of the host plant. Useful vectors include, but are not limited to, pKYLX6, pKYLX7 (52), pBI101, pCambia series of vectors (http colon//www dot cambia dot org dot au) and the GATEWAY series of plant vectors (53).

While a promoter or terminator sequence can be ligated to a DNA of interest prior to insertion into a vector, in other embodiments, a vector is selected that includes a promoter and/or terminator operable in the host cell into which the vector is to be inserted. The DNA of interest is cloned into the vector such that it is operably linked to the promoter and/or terminator present in the vector. For example, the vector may contain a promoter of the present invention upstream of a terminator of the present invention. The promoter and terminator are separated by a cloning site into which the DNA of interest is inserted.

In preparing the expression cassette, the various DNA fragments may be manipulated, so as to provide for the DNA sequences in the proper orientation and, as appropriate, in the proper reading frame. Toward this end, adapters or linkers may be employed to join the DNA fragments or other manipulations may be involved to provide for convenient restriction sites, removal of superfluous DNA, removal of restriction sites, or the like. For this purpose, in vitro mutagenesis, primer repair, restriction, annealing, resubstitutions, e.g. transitions and transversions may be involved.

Selectable Markers

Generally, the vectors will comprise a selectable marker gene for the selection of transformed cells. Selectable marker genes are utilized for the selection of transformed cells or tissues. Usually, the plant selectable marker gene will encode antibiotic resistance, with suitable genes including at least one set of genes coding for resistance to the antibiotic spectinomycin, the streptomycin phosphotransferase (spt) gene coding for streptomycin resistance, the aadA gene coding for spectinomycin and streptomycin resistance, the neomycin phosphotransferase (nptII) gene encoding kanamycin or geneticin resistance and the hygromycin phosphotransferase (hpt or aphiv) gene encoding resistance to hygromycin. Alternatively, the plant selectable marker gene will encode herbicide resistance such as resistance to the sulfonylurea-type herbicides, glufosinate, glyphosate, ammonium, bromoxynil, imidazolinones, and 2,4-dichlorophenoxyacetate (2,4-D), including genes coding for resistance to herbicides which act to inhibit the action of glutamine synthase such as phosphinothricin or basta (e.g., the bar gene), or acetolactate synthase (als) genes which encodes resistance to the herbicide chlorsulfuron. See generally, International Publication No. WO 02/36782, U.S. Pat. No. 7,205,453 and U.S. Patent Application Publication Nos. 2006/0248616 and 2007/0143880, and those references cited therein. This list of selectable marker genes is not meant to be limiting. Any selectable marker gene can be used.

Transformation of Host Cells

Once a nucleic acid has been cloned into an expression vector, it may be introduced into a plant cell using conventional transformation procedures. The term "plant cell" is intended to encompass any cell derived from a plant including undifferentiated tissues such as callus and suspension cultures, as well as plant seeds, pollen or plant embryos. Plant tissues suitable for transformation include leaf tissues, root tissues, meristems, protoplasts, hypocotyls, cotyledons, scutellum, shoot apex, root, immature embryo, pollen, and anther. "Transformation" means the directed modification of the genome of a cell by the external application of recombinant DNA from another cell of different genotype, leading to its uptake and integration into the subject cell's genome. In this manner, genetically modified plants, plant cells, plant tissue, seed, and the like can be obtained.

Transformation of a plant can be accomplished in a wide variety of ways within the scope of a person of ordinary skill in the art. Transformation protocols may vary depending on the type of plant or plant cell, i.e., monocot or dicot, targeted for transformation, as is well known to the skilled artisan. In one embodiment, a DNA construct is incorporated into a plant by (i) transforming a cell, tissue or organ from a host plant with the DNA construct; (ii) selecting a transformed cell, cell callus, somatic embryo, or seed which contains the DNA construct; (iii) regenerating a whole plant from the selected transformed cell, cell callus, somatic embryo, or seed; and (iv) selecting a regenerated whole plant that expresses the polynucleotide. Many methods of transforming a plant, plant tissue or plant cell for the construction of a transformed cell are suitable. Once transformed, these cells can be used to regenerate transgenic plants[54]. Those of ordinary skill in the art can use different plant gene transfer techniques found in references for but not limited to, the electroporation (55-59), microinjection (60, 61), lipofection (62), liposome or spheroplast fusions (63-65), *Agrobacterium* (66), direct gene transfer (67), T-DNA mediated transformation of monocots[6][(68)] or dicots (69, 70), microprojectile bombardment or ballistic particle acceleration (71-74), chemical transfection including $CaCl_2$ precipitation, polyvinyl alcohol, or poly-L-ornithine (75), silicon carbide whisker methods (76, 77), laser methods (78, 79), sonication methods (80-82), polyethylene glycol methods (83), vacuum infiltration (84), floral dip (85) and transbacter (86).

In one embodiment of the invention, a transformed host cell may be cultured to produce a transformed plant. In this regard, a transformed plant can be made, for example, by transforming a cell, tissue or organ from a host plant with an inventive DNA construct; selecting a transformed cell, cell callus, somatic embryo, or seed which contains the DNA construct; regenerating a whole plant from the selected transformed cell, cell callus, somatic embryo, or seed; and selecting a regenerated whole plant that expresses the polynucleotide.

A wide variety of plant cells may be used in the invention, including mosses, gymnosperms and flowering plants, Preferred host cells are crops from monocotyledons, such as corn, rice, sugarcane, rye grass, Bermuda grass, Blue grass, Fescue, wheat, sorghum or dicotyledons, including cotton, rapeseed, sugarbeet, camelina, soybean and tomatoes.

The foregoing methods for transformation are typically used for producing a transgenic variety in which the expression cassette is stably incorporated. After the expression cassette is stably incorporated in transgenic plants, it can be transferred to other plants by sexual crossing. In one embodiment, the transgenic variety could then be crossed, with another (non-transformed or transformed) variety, in order to produce a new transgenic variety. Alternatively, a genetic trait which has been engineered into a particular cotton line using the foregoing transformation techniques could be moved into another line using traditional backcrossing techniques that are well known in the plant breeding arts. For example, a backcrossing approach could be used to move an engineered trait from a public, non-elite variety into an elite variety, or from a variety containing a foreign gene in its genome into a variety or varieties which do not contain that gene. As used herein, "crossing" can refer to a simple X by Y cross, or the process of backcrossing, depending on the context. Any of a number of standard breeding techniques can be used, depending upon the species to be crossed.

Once transgenic plants of this type are produced, the plants themselves can be cultivated in accordance with conventional procedures. Transgenic seeds can, of course, be recovered from the transgenic plants. These seeds can then be planted in the soil and cultivated using conventional procedures to produce transgenic plants. The cultivated transgenic plants will express the DNA of interest in a tissue-preferred or tissue-specific manner as described herein.

Suitable Plants

The methods described above may be applied to transform a wide variety of plants, including decorative or recreational plants or crops, but are particularly useful for treating commercial and ornamental crops. Examples of plants that may be transformed in the present invention include, but are not limited to, Acacia, alfalfa, aneth, apple, apricot, artichoke, arugula, asparagus, avocado, banana, barley, beans, beech, beet, Bermuda grass, blackberry, blueberry, Blue grass, broccoli, Brussels sprouts, cabbage, camelina, canola, cantaloupe, carrot, cassava, cauliflower, celery, cherry, chicory, cilantro, citrus, clementines, coffee, corn, cotton, cucumber, duckweed, Douglas fir, eggplant, endive, escarole, eucalyptus, fennel, fescue, figs, forest trees, garlic, gourd, grape, grapefruit, honey dew, jatropha, jicama, kiwifruit, lettuce, leeks, lemon, lime, Loblolly pine, maize, mango, melon, mushroom, nectarine, nut, oat, okra, onion, orange, an ornamental plant, palm, papaya, parsley, pea, peach, peanut, pear, pepper, persimmon, pine, pineapple, plantain, plum, pomegranate, poplar, potato, pumpkin, quince, radiata pine, radicchio, radish, rapeseed, raspberry, rice, rye, rye grass, scallion, sorghum, Southern pine, soybean, spinach, squash, strawberry, sugarbeet, sugarcane, sunflower, sweet potato, sweetgum, switchgrass, tangerine, tea, tobacco, tomato, turf, turnip, a vine, watermelon, wheat, yams, and zucchini. Other suitable hosts include algae and other photosynthetic organisms.

DEFINITIONS

Unless defined otherwise, all technical and scientific terms used herein have the same meaning as is commonly understood by one of skill in the art to which the invention belongs.

The term "polynucleotide" refers to a natural or synthetic linear and sequential array of nucleotides and/or nucleosides, including deoxyribonucleic acid, ribonucleic acid, and derivatives thereof. It includes chromosomal DNA, self-replicating plasmids, infectious polymers of DNA or RNA and DNA or RNA that performs a primarily structural role. Unless otherwise indicated, nucleic acids or polynucleotide are written left to right in 5' to 3' orientation, Nucleotides are referred to by their commonly accepted single-letter codes. Numeric ranges are inclusive of the numbers defining the range.

The terms "amplified" and "amplification" refer to the construction of multiple copies of a nucleic acid sequence or multiple copies complementary to the nucleic acid sequence using at least one of the nucleic acid sequences as a template. Amplification can be achieved by chemical synthesis using any of the following methods, such as solid-phase phosphoramidate technology or the polymerase chain reaction (PCR). Other amplification systems include the ligase chain reaction system, nucleic acid sequence based amplification, Q-Beta Replicase systems, transcription-based amplification system, and strand displacement amplification. The product of amplification is termed an amplicon.

As used herein "promoter", "promoter region", or "promoter sequence" includes reference to a region of DNA upstream from the start of transcription and involved in recognition and binding of RNA polymerase, either I, II or III, and other proteins to initiate transcription. Promoters include necessary nucleic acid sequences near the start site of transcription, such as, in the case of a polymerase II type promoter, a TATA element. A promoter also optionally includes distal enhancer or repressor elements, which can be located as far as several thousand base pairs from the start site of transcription. In addition a promoter or promoter region includes variations of the promoter by inserting or deleting regulatory regions or motifs, altering the promoter by random or site-mutagenesis. The activity or strength of a promoter may be measured in terms of the amount of RNA or the amount of gene product or peptide in the cell, tissue or organ of the plant.

The term "plant promoter" refers to a promoter capable of initiating transcription in plant cells.

The term "foreign promoter" refers to a promoter, other than the native, or natural, promoter, which promotes transcription of a length of DNA of viral, bacterial or eukaryotic origin, including those from microbes, plants, plant viruses, invertebrates or vertebrates.

As used herein "terminator", "terminator region", or "terminator sequence" includes reference to a region of DNA downstream from the stop codon (usually TGA, TAG, TAA) in the open reading frame and involved in RNA processing. Terminators may include a polyadenylation sequence or cleavage site, NUEs or FUEs. Terminators enhance processing at the polyadenylation site and elements that increase the stability of the transcribed RNA. A terminator or terminator region includes variations of the terminator by inserting or deleting regulatory regions or motifs or altering the terminator by random or site-mutagenesis.

The term "microbe" refers to any microorganism (including both eukaryotic and prokaryotic microorganisms), such as fungi, yeast, bacteria, actinomycetes, algae and protozoa, as well as other unicellular structures.

The term "plant" includes whole plants, and plant organs, and progeny of same. Plant organs comprise, e.g., shoot vegetative organs/structures (e.g. leaves, stems and tubers), roots, flowers and floral organs/structures (e.g. bracts, sepals, petals, stamens, carpels, anthers and ovules), seed (including embryo, endosperm, and seed coat) and fruit (the mature ovary), plant tissue (e.g. vascular tissue, ground tissue, and the like) and cells (e.g. guard cells, egg cells, trichomes and the like). The class of plants that can be used in the method of the invention is generally as broad as the class of higher and lower plants amenable to transformation techniques, including angiosperms (monocotyledonous and dicotyledonous plants), gymnosperms, ferns, and multicellular algae. It includes plants of a variety of ploidy levels, including aneuploid, polyploid, diploid, haploid and hemizygous.

The term "constitutive" refers to a promoter that is active under most environmental and developmental conditions, such as, for example, but not limited to, the CaMV 35S promoter and the nos terminator.

The term "tissue-preferred promoter" refers to a promoter that is under developmental control or a promoter that preferentially initiates transcription in certain tissues.

The term "tissue-specific promoter" refers to a promoter that initiates transcription only in certain tissues.

The term "cell-type specific promoter" refers to a promoter that primarily initiates transcription only in certain cell types in one or more organs.

The term "inducible promoter" refers to a promoter that is under environmental control.

The terms "encoding" and "coding" refer to the processes by which a polynucleotide (i) through the mechanism of transcription provides a functional RNA, an antisense RNA or a sense RNA or (ii) through the mechanisms of transcription and translation provides the information to a cell from which a series of amino acids can be assembled into a specific amino acid sequence to produce a functional polypeptide, such as, for example, an active enzyme or ligand binding protein.

The terms "polypeptide," "peptide," "protein" and "gene product" are used interchangeably herein to refer to a polymer of amino acid residues. The terms apply to amino acid polymers in which one or more amino acid residue is an artificial chemical analogue of a corresponding naturally occurring amino acid, as well as to naturally occurring amino acid polymers. Amino acids may be referred to by their commonly known three-letter or one-letter symbols. Amino acid sequences are written left to right in amino to carboxy orientation, respectively. Numeric ranges are inclusive of the numbers defining the range.

The term "expression" refers to the transcription of a gene to produce the corresponding mRNA and translation of this mRNA to produce the corresponding gene product (i.e., a peptide, polypeptide, or protein) and activity of the protein to confer a function. "Expression" refers to the transcription of a gene to produce a functional RNA.

The term "antisense RNA" refers to the transcription of a region of DNA to produce an RNA molecule capable of hybridizing to a second RNA molecule. Those of ordinary skill in the art can make antisense RNA by expressing the inverse complement of a gene or gene segment.

The term "gene" refers to chromosomal or genomic DNA, plasmid DNA, cDNA, synthetic DNA, or other DNA that transcribes a functional RNA molecule or encodes a peptide, polypeptide, or protein.

The term "recombinant" includes reference to a cell or vector that has been modified by the introduction of a heterologous nucleic acid. Recombinant cells express genes that are not normally found in that cell or express native genes that are otherwise abnormally expressed, underexpressed, or not expressed at all as a result of deliberate human intervention, or expression of the native gene may have reduced or eliminated as a result of deliberate human intervention.

The term "recombinant expression cassette" refers to a nucleic acid construct, generated recombinantly or synthetically, with a series of specified nucleic acid elements, which permit transcription of a particular nucleic acid in a target cell. The recombinant expression cassette can be incorporated into a plasmid, chromosome, mitochondrial DNA, plastid DNA, virus, or nucleic acid fragment. Typically, the recombinant expression cassette portion of an expression vector includes, among other sequences, a nucleic acid to be transcribed, and a promoter.

The term "similar construct" as used herein means a construct that also has codon optimization in the DNA of interest and is further modified in the nucleotide sequence around the start codon to optimize expression in transgenic plants (98, 99).

The term "open reading frame" (ORF) is a polynucleotide that is translated into a peptide by ribosomes. Nucleotides in the ORF are translated by groups of three nucleotides, called codons, into amino acid residues that are incorporated into the peptide or protein. Translation of the ORF begins at the initiation site or start codon (ATG) and ends with termination codon (TGA, TAG, TAA). Some mitochondrial and bacterial genomes diverge from the universal codon usage, e.g., some termination codons in the universal code specify amino acids in the mitochondria or bacterial.

The term "functional RNA" includes non-coding RNA with include transfer RNA (tRNA), ribosomal RNA (rRNA), small nucleolar RNAs (snoRNAs), microRNAs (miRNAs), double stranded RNA (dsRNA) and small interfering RNA (siRNA) which may be a double stranded molecule or may be a short hairpin RNA (shRNA).

The term "transgenic plant" includes reference to a plant, which comprises within its genome a heterologous polynucleotide. Generally, the heterologous polynucleotide is integrated within the genome such that the polynucleotide is passed on to successive generations. The heterologous polynucleotide may be integrated into the genome alone or as part of a recombinant expression cassette. "Transgenic" is also used to include any cell, cell line, callus, tissue, plant part or plant, the genotype of which has been altered by the presence of heterologous nucleic acid including those transgenic plants altered or created by sexual crosses or asexual propagation from the initial transgenic plant. In addition "transgenic" comprises plants that contain within its genome a homologous polynucleotide that was transferred into the plant by transformation event. The term "transgenic" does not encompass the alteration of the genome by conventional plant breeding methods or by naturally occurring events such as random cross-fertilization, non-recombinant viral infection, non-recombinant bacterial transformation, non-recombinant transposition, or spontaneous mutation.

The term "vector" includes reference to a nucleic acid used in transfection or transformation of a host cell and into which can be inserted a polynucleotide.

The term "selectively hybridizes" includes reference to hybridization, under stringent hybridization conditions, of a nucleic acid sequence to a specified nucleic acid target sequence to a detectably greater degree (e.g., at least 2-fold over background) than its hybridization to non-target nucleic acid sequences and to the substantial exclusion of non-target nucleic acids. Selectively hybridizing sequences typically have about at least 40% sequence identity, preferably 60-90% sequence identity, and most preferably 100% sequence identity (i.e., complementary) with each other.

The terms "stringent conditions" and "stringent hybridization conditions" include reference to conditions under which a probe will hybridize to its target sequence, to a detectably greater degree than other sequences (e.g., at least 2-fold over background). Stringent conditions are sequence-dependent and will be different in different circumstances. By controlling the stringency of the hybridization and/or washing conditions, target sequences can be identified which can be up to 100% complementary to the probe (homologous probing). Alternatively, stringency conditions can be adjusted to allow some mismatching in sequences so that lower degrees of similarity are detected (heterologous probing). Optimally, the probe is approximately 500 nucleotides in length, but can vary greatly in length from less than 500 nucleotides to equal to the entire length of the target sequence.

Typically, stringent conditions will be those in which the salt concentration is less than about 1.5 M Na ion, typically about 0.01 to 1.0 M Na ion concentration (or other salts) at pH 7.0 to 8.3 and the temperature is at least about 30° C. for short probes (e.g., 10 to 50 nucleotides) and at least about 60° C. for long probes (e.g., greater than 50 nucleotides). Stringent conditions may also be achieved with the addition of destabilizing agents such as formamide or Denhardt's. Low stringency conditions include hybridization with a buffer solution of 30 to 35% formamide, 1 M NaCl, 1% SDS (sodium dodecyl sulfate) at 37° C., and a wash in 1× to 2×SSC (20×SSC=3.0 M NaCl/0.3 M trisodium citrate) at 50 to 55° C. Moderate stringency conditions include hybridization in 40 to 45% formamide, 1 M NaCl, 1% SDS at 37° C., and a wash in 0.5× to 1×SSC at 55 to 60° C. High stringency conditions include hybridization in 50% formamide, 1 M NaCl, 1% SDS at 37° C., and a wash in 0.1×SSC at 60 to 65° C. Specificity is typically the function of post-hybridization washes, the critical factors being the ionic strength and temperature of the final wash solution. For DNA-DNA hybrids, the $T_m$ can be approximated[87], where the $T_m$=81.5° C.+16.6 (log M)+0.41 (% GC)−0.61 (% form)−500/L; where M is the molarity of monovalent cations, % GC is the percentage of guanosine and cytosine nucleotides in the DNA, % form is the percentage of formamide in the hybridization solution, and L is the length of the hybrid in base pairs. $T_m$ is the temperature (under defined ionic strength and pH) at which 50% of a complementary target sequence hybridizes to a perfectly matched probe. $T_m$ is reduced by about 1° C. for each 1% of mismatching; thus, $T_m$, hybridization and/or wash conditions can be adjusted to hybridize to sequences of the desired identity. For example, if sequences with ≥90% identity are sought, the $T_m$ can be decreased 10° C. Generally, stringent conditions are selected to be about 5° C. lower than the thermal melting point ($T_m$) for the specific sequence and its complement at a defined ionic strength and pH. However, severely stringent conditions can utilize a hybridization and/or wash at 1, 2, 3 or 4° C. lower than the thermal melting point ($T_m$); moderately stringent conditions can utilize a hybridization and/or wash at 6, 7, 8, 9 or 10° C. lower than the thermal melting point ($T_m$); low stringency conditions can utilize a hybridization and/or wash at 11, 12, 13, 14, 15 or 20° C. lower than the thermal melting point ($T_m$). Using the equation, hybridization and wash compositions, and desired $T_m$, those of ordinary skill in the art will understand that variations in the stringency of hybridization and/or wash solutions are inherently described. An extensive guide to the hybridization of nucleic acids is found in the scientific literature[88,89] Unless otherwise stated, in the present application high stringency is defined as hybridization in 4×SSC, 5×Denhardt's (5 g Ficoll, 5 g polyvinypyrrolidone, 5 g bovine serum albumin in 500 ml of water), 0.1 mg/ml boiled salmon sperm DNA, and 25 mM Na phosphate at 65° C., and a wash in 0.1×SSC, 0.1% SDS at 65° C.

The following terms are used to describe the sequence relationships between two or more nucleic acids: "reference sequence," "comparison window," "sequence identity," "percentage of sequence identity," and "substantial identity."

The term "reference sequence" is a defined sequence used as a basis for sequence comparison. A reference sequence may be a subset or the entirety of a specified sequence; for example, as a segment of a regulatory sequence (promoter or terminator) of the invention or a segment of the regulatory sequence.

The term "comparison window" includes reference to a contiguous and specified segment of a polynucleotide sequence, where the polynucleotide sequence may be compared to a reference sequence and the portion of the polynucleotide sequence in the comparison window may comprise additions or deletions (i.e., gaps) when it is compared to the reference sequence for optimal alignment. The comparison window is usually at least 20 contiguous nucleotides in length, and optionally can be 30, 40, 50, 100 or longer. Those of ordinary skill in the art understand that the inclusion of gaps in a polynucleotide sequence alignment introduces a gap penalty, and it is subtracted from the number of matches.

Methods of alignment of a nucleotide for comparison are well known to those of ordinary skill in the art. The local homology algorithm, BESTFIT (90), can perform an optimal alignment of sequences for comparison using a homology alignment algorithm called GAP (91), search for similarity using Tfasta and Fasta (92), by computerized implementations of these algorithms widely available online or from various vendors (Intelligenetics, Genetics Computer Group). CLUSTAL allows for the alignment of multiple sequences (93-95) and program PileUp can be used for optimal global alignment of multiple sequences (96). The BLAST family of programs can be used for nucleotide or protein database similarity searches. BLASTN searches a nucleotide database using a nucleotide query.

GAP (91) maximizes the number of matches and minimizes the number of gaps in an alignment of two complete sequences. GAP considers all possible alignments and gap positions and creates the alignment with the largest number of matched bases and the fewest gaps. It also calculates a gap penalty and a gap extension penalty in units of matched bases. Default gap creation penalty values and gap extension penalty values in Version 10 of the Wisconsin Genetics Software Package are 8 and 2, respectively. The gap creation and gap extension penalties can be expressed as an integer selected from the group of integers consisting of from 0 to 100. GAP displays four figures of merit for alignments: Quality, Ratio, Identity, and Similarity. The Quality is the metric maximized in order to align the sequences. Ratio is the quality divided by the number of bases in the shorter segment. Percent Identity is the percent of the symbols that actually match. Percent Similarity is the percent of the symbols that are similar. Symbols that are across from gaps are ignored. A similarity is scored when the scoring matrix value for a pair of symbols is greater than or equal to 0.50, the similarity threshold. The scoring matrix used in Version 10 of the Wisconsin Genetics Software Package is BLOSUM62 (97).

The terms "sequence identity" and "identity" are used in the context of two nucleic acid sequences and include reference to the residues in the two sequences, which are the same when aligned for maximum correspondence over a specified comparison window.

The term "percentage of sequence identity" means the value determined by comparing two optimally aligned sequences over a comparison window, wherein the portion of the polynucleotide sequence in the comparison window may comprise gaps (additions or deletions) when compared to the reference sequence for optimal alignment. The percentage is calculated by determining the number of positions at which the identical nucleic acid base or amino acid residue occurs in both sequences to yield the number of matched positions, dividing the number of matched positions by the total number of positions in the window of comparison and multiplying the result by 100 to yield the percentage of sequence identity.

The term "substantial identity" of polynucleotide sequences means that a polynucleotide comprises a sequence that has between 50-100% sequence identity, preferably at least 50% sequence identity, preferably at least 60% sequence identity, preferably at least 70%, more preferably at least 80%, more preferably at least 90%, and most preferably at least 95%, compared to a reference sequence using one of the alignment programs described using standard parameters. One of ordinary skill in the art will recognize that these values can be appropriately adjusted to determine corresponding identity of two nucleotide sequences.

Another indication that nucleotide sequences are substantially identical is if two molecules hybridize to each low stringency conditions, moderate stringency conditions or high stringency conditions.

The practice of the present invention employs, unless otherwise indicated, conventional techniques of chemistry, molecular biology, microbiology, recombinant DNA, genetics, immunology, cell biology, cell culture and transgenic biology, which are within the skill of the art. See, e.g., Maniatis et al., 1982, *Molecular Cloning* (Cold Spring Harbor Laboratory Press, Cold Spring Harbor, N.Y.); Sambrook et al., 1989, *Molecular Cloning*, 2nd Ed. (Cold Spring Harbor Laboratory Press, Cold Spring Harbor, N.Y.); Sambrook and Russell, 2001, *Molecular Cloning*, 3rd Ed. (Cold Spring Harbor Laboratory Press, Cold Spring Harbor, N.Y.); Ausubel et al., 1992), *Current Protocols in Molecular Biology* (John Wiley & Sons, including periodic updates); Glover, 1985, *DNA Cloning* (IRL Press, Oxford); Russell, 1984, *Molecular biology of plants: a laboratory course manual* (Cold Spring Harbor Laboratory Press, Cold Spring Harbor, N.Y.); Anand, *Techniques for the Analysis of Complex Genomes*, (Academic Press, New York, 1992); Guthrie and Fink, *Guide to Yeast Genetics and Molecular Biology* (Academic Press, New York, 1991); Harlow and Lane, 1988, *Antibodies*, (Cold Spring Harbor Laboratory Press, Cold Spring Harbor, N.Y.); *Nucleic Acid Hybridization* (B. D. Hames & S. J. Higgins eds. 1984); *Transcription And Translation* (B. D. Hames & S. J. Higgins eds. 1984); *Culture Of Animal Cells* (R. I. Freshney, Alan R. Liss, Inc., 1987); *Immobilized Cells And Enzymes* (IRL Press, 1986); B. Perbal, *A Practical Guide To Molecular Cloning* (1984); the treatise, *Methods In Enzymology* (Academic Press, Inc., N.Y.); *Methods In Enzymology*, Vols. 154 and 155 (Wu et al. eds.), *Immunochemical Methods In Cell And Molecular Biology* (Mayer and Walker, eds., Academic Press, London, 1987); *Handbook Of Experimental Immunology*, Volumes I-IV (D. M. Weir and C. C. Blackwell, eds., 1986); Riott, *Essential Immunology*, 6th Edition, Blackwell Scientific Publications, Oxford, 1988; Fire et al., *RNA Interference Technology: From Basic Science to Drug Development*, Cambridge University Press, Cambridge, 2005; Schepers, *RNA Interference in Practice*, Wiley-VCH, 2005; Engelke, *RNA Interference (RNAi): The Nuts & Bolts of siRNA Technology*, DNA Press, 2003; Gott, *RNA Interference, Editing, and Modification: Methods and Protocols (Methods in Molecular Biology)*, Human Press, Totowa, N.J., 2004; Sohail, *Gene Silencing by RNA Interference: Technology and Application*, CRC, 2004.

EXAMPLES

The present invention is described by reference to the following Examples, which are offered by way of illustration and are not intended to limit the invention in any manner. Standard techniques well known in the art or the techniques specifically described below were utilized.

Example 1

Development of a Transgenic Plant with the Regulatory Sequences of the Invention Expressing a Peptide in Leaves Step 1: Use chemical synthesis to make a DNA construct that contains a promoter (SEQ ID NO:1) with a gene or a coding sequence for gamma-aminobutyraldehyde dehydrogenase (GALD) using the following nucleotides: by 1497760 to by 1499184 of locus AP012030 or by 1 to by 1503 of locus NZ_ACGG01000118 and a terminator (SEQ ID NO: 2). Clone the DNA construct into a binary vector, such as pCambia1300, pCambia2300 or pCambia3200.

Step 2: Transform the DNA construct into *Agrobacterium tumefaciens*, select for antibiotic resistance and confirm the presence of the DNA construct.

Step 3: Transform a plant (*Arabidopsis*, soybean, corn, camelina, canola, rice, cotton, wheat, sugarbeet, sugarcane, or sorghum) and select for transgenic plants. Confirm the presence of the DNA constructs in the transgenic plants.

Example 2

Development of a Transgenic Plant with the Regulatory Sequences of the Invention Expressing a Peptide, Using a Promoter Truncated on the 5' End Step 1: Use chemical synthesis to make a DNA construct that contains a promoter (SEQ ID NO:3) with a gene or a coding sequence for putrescine aminotransferase (PAT) using the nucleotides by 1 to by 1380 of locus NZ_ACGCr01000104 or the nucleotides "ATO" followed by the nucleotides by 3197400 to by 3198779 of locus AP012030, and a terminator (SEQ ID NO: 2). Clone the DNA construct into a binary vector, such as pCambia1300, pCambia2300 or pCambia3200.

Step 2: Transform the DNA construct into *Agrobacterium tumefaciens*, select for antibiotic resistance and confirm the presence of the DNA construct.

Step 3: Transform a plant (*Arabidopsis*, soybean, corn, camelina, canola, rice, cotton, wheat, sugar beet, sugarcane, or sorghum), select for transgenic plants. Confirm the presence of the DNA constructs in the transgenic plants.

Example 3

Development of a Transgenic Plant with the Regulatory Sequences of the Invention Expressing a Peptide, Using a Promoter Significantly Truncated on the 5' End Step 1: Use chemical synthesis to make a DNA construct that contains a promoter (SEQ ID NO:4) with a gene or a coding sequence for cysteine dioxygenase (CDO) using the nucleotides from by 22 to by 627 of locus NM_200741 or the gene for sulfinic acid decarboxylase (SAD) using the nucleotides from by 107 to by 1555 of locus NM_001007348, and a terminator (SEQ ID NO: 2). Clone the DNA construct into a binary vector, such as pCambia1300, pCambia2300 or pCambia3200.

Step 2: Transform the DNA construct into *Agrobacterium tumefaciens*, select for antibiotic resistance and confirm the presence of the DNA construct.

Step 3: Transform a plant (*Arabidopsis*, soybean, corn, camelina, canola, rice, cotton, wheat, sugar beet, sugarcane, or sorghum), select for transgenic plants. Confirm the presence of the DNA constructs in the transgenic plants.

Example 4

Development of a Transgenic Plant with the Regulatory Sequences of the Invention Expressing a Peptide, Using a Promoter Truncated on the 3' End Step 1: Use chemical synthesis to make a DNA construct that contains a promoter (SEQ ID NO:5) with a gene or a coding sequence for taurine dioxygenase (TDO) using the nucleotides by 388219 to by 389070 of locus AP012030, and a terminator (SEQ ID NO: 2). Clone the DNA construct into a binary vector, such as pCambia1300, pCambia2300 or pCambia3200.

Step 2: Transform the DNA construct into *Agrobacterium tumefaciens*, select for antibiotic resistance and confirm the presence of the DNA construct.

Step 3: Transform a plant (*Arabidopsis*, soybean, corn, camelina, canola, rice, cotton, wheat, sugar beet, sugarcane, or sorghum), select for transgenic plants. Confirm the presence of the DNA constructs in the transgenic plants.

Example 5

Development of a Transgenic Plant with the Regulatory Sequences of the Invention Expressing a Peptide, Using a Promoter Truncated on the 5' and 3' Ends Step 1: Use chemical synthesis to make a DNA construct that contains a promoter (SEQ ID NO:6 or SEQ ID NO:7) with a gene or coding sequence for taurine-pyruvate aminotransferase (TPAT) using the nucleotides from by complement 947668 to 946277 of locus CP000362 or truncated glutamate/aspartate periplasmic binding protein (trGABP) using the nucleotides "ATG" followed by the nucleotides from by 2953489 to by 2954313 of locus CP002167, and a terminator (SEQ ID NO:2). Clone the DNA construct into a binary vector, such as pCambia1300, pCambia2300 or pCambia3200.

Step 2: Transform the DNA construct into *Agrobacterium tumefaciens*, select for antibiotic resistance and confirm the presence of the DNA construct.

Step 3: Transform a plant (*Arabidopsis*, soybean, corn, camelina, canola, rice, cotton, wheat, sugar beet, sugarcane, or sorghum), select for transgenic plants. Confirm the presence of the DNA constructs in the transgenic plants.

Example 6

Development of a Transgenic Plant with the Regulatory Sequences of the Invention Expressing a Peptide in Vascular Tissue Step 1: Use chemical synthesis to make a DNA construct that contains a promoter (SEQ ID NO:8) with a gene or coding sequence for PAT, GALD, CDO, SAD, TDO or trGABP and a terminator (SEQ ID NO:9). Clone the DNA construct into a binary vector, such as pCambia1300, pCambia2300 or pCambia3200.

Step 2: Transform the DNA construct into *Agrobacterium tumefaciens*, select for antibiotic resistance and confirm the presence of the DNA construct.

Step 3: Transform a plant (*Arabidopsis*, soybean, corn, camelina, canola, rice, cotton, wheat, sugarbeet, sugarcane, or sorghum) and select for transgenic plants. Confirm the presence of the DNA constructs in the transgenic plants.

Example 7

Development of a Transgenic Plant with the Regulatory Sequences of the Invention Expressing a Peptide in Vascular Tissue a Promoter Truncated on the 5' End Step 1: Use chemical synthesis to make a DNA construct that contains a promoter (SEQ ID NO:10 or SEQ ID NO:11)

with the gene for PAT, GALD, CDO, SAD, TDO or trGABP, and a terminator (SEQ ID NO: 9). Clone the DNA construct into a binary vector, such as pCambia1300, pCambia2300 or pCambia3200.

Step 2: Transform the DNA construct into *Agrobacterium tumefaciens*, select for antibiotic resistance and confirm the presence of the DNA construct.

Step 3: Transform a plant (*Arabidopsis*, soybean, corn, camelina, canola, rice, cotton, wheat, sugarbeet, sugarcane, or sorghum) and select for transgenic plants. Confirm the presence of the DNA constructs in the transgenic plants.

Example 8

Development of a Transgenic Plant with the Regulatory Sequences of the Invention Expressing a Peptide in Leaves Step 1: Use chemical synthesis to make a DNA construct that contains a promoter (SEQ ID NO:1) with a gene or a coding sequence for GALD and the terminator of the octopine synthase (ocs) gene (34). Clone the DNA construct into a binary vector, such as pCambia1300, pCambia2300 or pCambia3200.

Step 2: Transform the DNA construct into *Agrobacterium tumefaciens*, select for antibiotic resistance and confirm the presence of the DNA construct.

Step 3: Transform a plant (*Arabidopsis*, soybean, corn, camelina, canola, rice, cotton, wheat, sugarbeet, sugarcane, or sorghum) and select for transgenic plants. Confirm the presence of the DNA constructs in the transgenic plants.

Example 9

Development of a Transgenic Plant with the Regulatory Sequences of the Invention Expressing a Peptide in Vascular Tissue Step 1: Use chemical synthesis to make a DNA construct that contains a promoter (SEQ ID NO: 8) with a gene or coding sequence for PAT and the terminator of the nopaline synthase (nos) gene (33). Clone the DNA construct into a binary vector, such as pCambia1300, pCambia2300 or pCambia3200.

Step 2: Transform the DNA construct into *Agrobacterium tumefaciens*, select for antibiotic resistance and confirm the presence of the DNA construct.

Step 3: Transform a plant (*Arabidopsis*, soybean, corn, camelina, canola, rice, cotton, wheat, sugarbeet, sugarcane, or sorghum) and select for transgenic plants. Confirm the presence of the DNA constructs in the transgenic plants.

Example 10

Development of a Transgenic Plant with the Regulatory Sequences of the Invention Expressing a Peptide in Corn Leaves To determine the functionality of the regulatory sequences in a monocot, corn, the regulatory sequences of the invention were identified based on their proximity to a putative gene in rice (LOC_Os02g07770.1). The alleged gene product is a potential ortholog to a transcription factor in *Arabidopsis* (At1g79430).

A search on the Rice Database (on Feb. 18, 2009 and again on Mar. 31, 2011) to determine the expression of the putative rice gene showed that there is no expressed sequence tag (EST) for LOC_Os02g07770.1 (http colon// rice dot plantbiology dot msu dot edu/expression underscore expression.shtml). Further analysis with Gene Expression Anatomy Viewer and Digital Northern (http colon//rice dot plantbiology dot msu dot edu/expression underscore anatomy.shtml) on the Rice Database showed no expression pattern for LOC_Os02g07770.1 in rice. The results from the combined analyses suggest that LOC_Os02g07770.1 is not expressed in rice and that the regulatory sequences of the invention are not functional.

Figure 2:
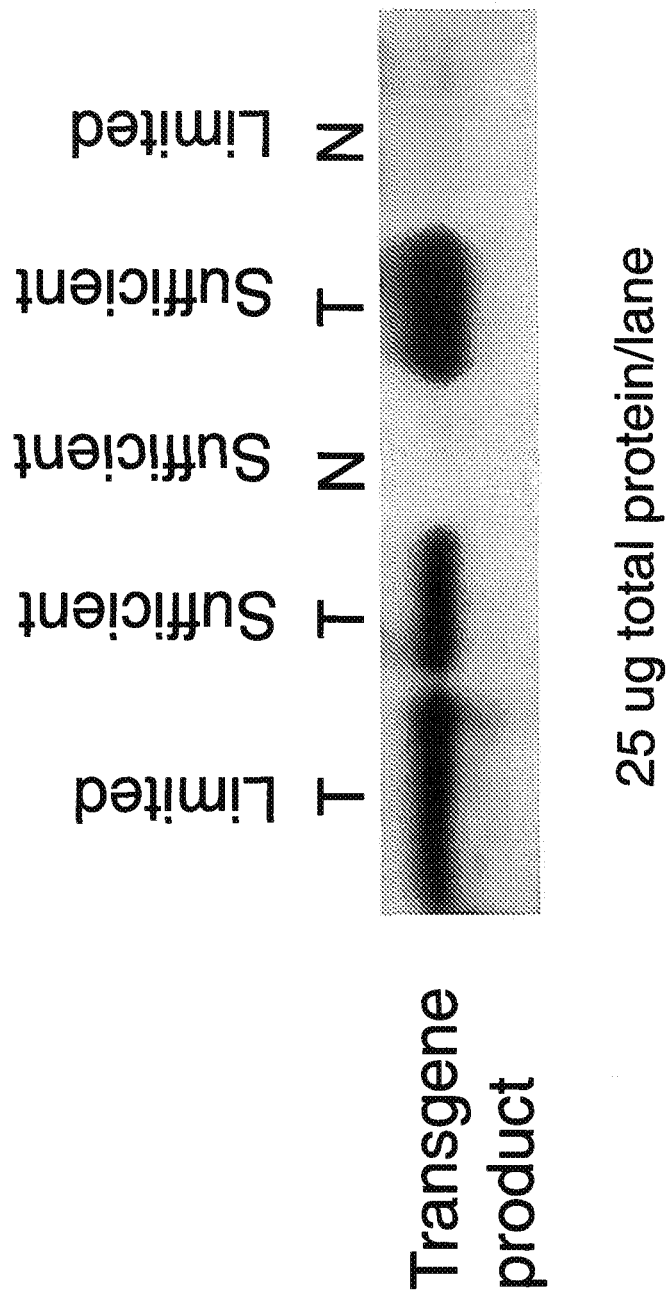
FIG. 2. Results of an immunoblot analysis to show the accumulation of a transgene product using a set of regulatory sequences of the invention in a segregating population of corn. The transgene product increases only in transgenic plants (T), not in non-transgenic siblings or nulls (N) when the plants are grown in either limited nutrient (Limited) or sufficient nutrient (Sufficient) conditions.

To determine if the regions flanking LOC_Os02g07770.1 are functional 5' and 3' regulatory sequences in plants they were operatively linked to the gene for GALD to prepare a similar construct to that described in Example 1. The gene construct was transferred into corn after sequence confirmation. Transgenic corn plants were selected and the presence of the gene construct was confirmed by PCR. Siblings (3 transgenic and 2 null controls) were grown on limited nutrient or sufficient nutrient conditions. The null-control plants are siblings of the transgenic plants that do not contain the transgenes. The sibling plants were grown in six-inch circular plastic pots. For the limited nutrient conditions the pots were filled with 600 g of 3 parts vermiculite and 1 part soil (Metro-Mix 360, Sun Gro Horticulture, USA). For the sufficient nutrient conditions the pots were filled with 600 g of a soil/peat mix (Metro-Mix 360, Sun Gro Horticulture, USA). The plants were maintained at 25° C., under compact fluorescent lights (450 umol of photons per $m^2$ per s) with a 16-h light/8-h dark cycle). The plants were watered as necessary by sub-irrigation. At day 30 proteins were extracted from approximately 500 mg of fresh leaf tissue. In one mL of extraction buffer which contained 50 mM Tris-HCl, pH 8.0, 1 mM EDTA, 5% (v/v) glycerol, 0.05% [v/v] Triton X-100, 0.5% [w/v] PVP-40 and Complete Protease Inhibitor Cocktail (Roche) protease inhibitor. The samples were incubated on ice for 15 to 30 mM. Debris was removed from the sample by centrifugation at 13,000×g for 10 min. Protein concentrations were determined. An equal amount (25 ug) of protein was added per lane. Proteins were separated by SDS-PAGE in a 10% polyacrylamide gel, blotted onto nitrocellulose and the transgene product was detected with anti-sera to GALD using chemiluminescence and X-ray film. FIG. 2 show that the transgenic plants accumulate the transgene product, showing that the 5' and 3' regions function as promoter and terminator, respectively, in corn. These findings show that the 5' and 3' regulatory sequences of the invention are functional in plants. These findings are unexpected in view of the apparent lack of expression of the putative gene in rice as determined from the database analysis described above.

The use of the terms "a" and "an" and "the" and similar referents in the context of describing the invention (especially in the context of the following claims) are to be construed to cover both the singular and the plural, unless otherwise indicated herein or clearly contradicted by context. The terms "comprising," "having," "including," and "containing" are to be construed as open-ended terms (i.e., meaning "including, but not limited to,") unless otherwise noted. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

Embodiments of this invention are described herein, including the best mode known to the inventors for carrying out the invention. Variations of those embodiments may become apparent to those of ordinary skill in the art upon reading the foregoing description. The inventors expect skilled artisans to employ such variations as appropriate, and the inventors intend for the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context. Embodiments of this invention are described herein, including the best mode known to the inventors for carrying out the invention. Variations of those embodiments may become apparent to those of ordinary skill in the art upon reading the foregoing description. The inventors expect skilled artisans to employ such variations as appropriate, and the inventors intend for the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

BIBLIOGRAPHY

1. Rombauts, S, Florquin, K, Lescot, M et al., 2003. Computational approaches to identify promoters and cis-regulatory elements in plant genomes. Plant Physiol, 132: 1162-76.
2. Molina, C & Grotewold, E 2005. Genome-wide analysis of *Arabidopsis* core promoters. BMC Genomics, 6: 25.
3. Yamamoto, Y Y, Ichida, H, Matsui, M et al., 2007. Identification of plant promoter constituents by analysis of local distribution of short sequences. BMC Genomics, 8: 67.
4. Bernard, V, Brunaud, V & Lecharny, A 2010. TC-motifs at the TATA-box expected position in plant genes: a novel class of motifs involved in the transcription regulation. BMC Genomics, 11: 166.
5. Stormo, G D 2000. Gene-finding approaches for eukaryotes. Genome Res, 10: 394-397.
6. Xie, F & Zhang, B 2010. Target-align: a tool for plant microRNA target identification. Bioinformatics (Oxford), 26: 3002-3003.
7. Moon, H & Callahan, A M 2004. Developmental regulation of peach ACC oxidase promoter-GUS fusions in transgenic tomato fruits. J Exp Bot, 55: 1519-1528.
8. Yang, S H, Yu, H & Goh, C J 2002. Isolation and characterization of the orchid cytokinin oxidase DSCKX1 promoter. J Exp Bot, 53: 1899-1907.
9. Wu, A-M, Lv, S-Y & Liu, J-Y 2007. Functional analysis of a cotton glucuronosyltransferase promoter in transgenic tobaccos. Cell Res, 17: 174-183.
10. Avsian-Kretchmer, O, Gueta-Dahan, Y, Lev-Yadun, S et al., 2004. The salt-stress signal transduction pathway that activates the gpx1 promoter is mediated by intracellular $H_2O_2$, different from the pathway induced by extracellular $H_2O_2$. Plant Physiol, 135: 1685-96.
11. Pathirana, M S, Samac, D A, Roeven, R et al., 1997. Analyses of phosphoenolpyruvate carboxylase gene structure and expression in alfalfa nodules. Plant J, 12: 293-304.
12. Dickey, L F, Gallo-Meagher, M & Thompson, W F 1992. Light regulatory sequences are located within the 5' portion of the Fed-1 message sequence. EMBO (Eur Mol Biol Organ) J, 11: 2311-2317.
13. Dickey, L F, Petracek, M E, Nguyen, T T et al., 1998. Light regulation of Fed-1 mRNA requires an element in the 5' untranslated region and correlates with differential polyribosome association. Plant Cell, 10: 475-484.
14. Caspar, T & Quail, P H 1993. Promoter and leader regions involved in the expression of the *Arabidopsis* ferredoxin A gene. The Plant Journal, 3: 161-174.
15. Bovy, A, Van Den Berg, C, De Vrieze, G et al., 1995. Light-regulated expression of the *Arabidopsis thaliana* ferredoxin gene requires sequences upstream and downstream of the transcription initiation site. Plant Mol Biol, 27: 27-39.
16. Hua, X J, Van de Cotte, B, Van Montagu, M et al., 2001. The 5' untranslated region of the At-P5R gene is involved in both transcriptional and post-transcriptional regulation. The Plant Journal, 26: 157-169.
17. Bolle, C, Sopory, S, Lubberstedt, T et al., 1994. Segments encoding 5'-untranslated leaders of genes for thylakoid proteins contain cis-elements essential for transcription. The Plant Journal, 6: 513-523.
18. Anderson, M B, Folta, K, Warpeha, K M et al., 1999. Blue light-directed destabilization of the pea Lhcb1*4 transcript depends on sequences within the 5' untranslated region. Plant Cell, 11: 1579-1589.
19. Fütterer, J & Hohn, T 1996. Translation in plants—rules and exceptions. Plant Mol Biol, 32: 159-189.
20. Gallie, D R 1996. Translational control of cellular and viral mRNAs. Plant Mol Biol, 32: 145-158.
21. Nagaya, S, Kawamura, K, Shinmyo, A et al., 2010. The HSP terminator of *Arabidopsis thaliana* Increases Gene Expression in Plant Cells. Plant Cell Physiol, 51: 328-332.
22. Mogen, B D, MacDonald, M H, Graybosch, R et al., 1990. Upstream sequences other than AAUAAA, are required for efficient messenger RNA 3'-end formation in plants. Plant Cell, 2: 1261-1272.
23. Mogen, B D, MacDonald, M H, Leggewie, G et al., 1992. Several distinct types of sequence elements are required for efficient mRNA 3' end formation in a pea rbcS gene. Molecular and Cellular Biology, 12: 5406-5414.
24. Rothnie, H M, Reid, J & Hahn, T 1994. The contribution of AAUAAA and the upstream element UUUGUA to the efficiency of mRNA 3'-end formation in plants. EMBO (Eur Mol Biol Organ) J, 13: 2200-2210.
25. Bassett, C L 2007. Regulation of Gene Expression in Plants: The Role of Transcript Structure and Processing. New York: Springer Press.
26. Ohme-Takagi, M, Taylor, C B, Newman, T C et al., 1993. The effect of sequences with high AU content on mRNA stability in tobacco. Proc Natl Acad Sci USA, 90: 11811-5.
27. Newman, T C, Ohme-Takagi, M, Taylor, C B et al., 1993. DST sequences, highly conserved among plant SAUR genes, target reporter transcripts for rapid decay in tobacco. Plant Cell, 5: 701-14.

28. Gutiérrez, R A, Macintosh, G C & Green, P J 1999. Current perspectives on mRNA stability in plants: multiple levels and mechanisms of control. Trends Plant Sci, 4: 429-438.
29. Ingelbrecht, I L, Herman, L M, Dekeyser, R A et al., 1989. Different 3' end regions strongly influence the level of gene expression in plant cells. Plant Cell, 1: 671-680.
30. An, G, Mitra, A, Choi, H K et al., 1989. Functional analysis of the 3' control region of the potato wound-inducible proteinase inhibitor II gene. Plant Cell, 1: 115-122.
31. Hudspeth, R L, Grula, J W, Dai, Z et al., 1992. Expression of maize phosphoenolpyruvate carboxylase in transgenic tobacco: Effects on biochemistry and physiology. Plant Physiol, 98: 458-464.
32. Mitsuhara, I, Ugaki M, Hirochika H et al., 1996. Efficient promoter cassettes for enhanced expression of foreign genes in dicotyledonous and monocotyledonous plants. Plant Cell Physiol, 37: 49-59.
33. Bevan, M, Barnes, W & Chilton, M D 1983. Structure and transcription of the nopaline synthase gene region of T-DNA. Nucleic Acids Res, 11: 369-385.
34. De Greve, H, Dhaese, P, Seurinck, J et al., 1982. Nucleotide sequence and transcript map of the *Agrobacterium tumefaciens* Ti plasmid-encoded octopine synthase gene. Journal of Molecular and Applied Genetics, 1: 499-511.
35. Keil, M, Sanchez-Serrano, J, Schell, J et al., 1986. Primary structure of a proteinase inhibitor II gene from potato (*Solanum tuberosum*). Nucleic Acids Res, 14: 5641-5650.
36. de Framond, A J 1991. A metallothionein-like gene from maize (*Zea mays*). Cloning and characterization. FEBS Lett, 290: 103-6.
37. Hudspeth, R L, Hobbs, S L, Anderson, D M et al., 1996. Characterization and expression of metallothionein-like genes in cotton. Plant Mol Biol, 31: 701-5.
38. Herrera-Estrella, L, Depicker, A, van Montagu, M et al., 1983. Expression of chimeric genes transferred into plant cells using a Ti-plasmid-derived vector. Nature, 303: 209-213.
39. Langenheim, J H & Thimann, K V 1982. Botany: Plant Biology and its Relation to Human Affairs. New York: John Wiley & Sons Inc.
40. Vasil, I K 1984. Cell Culture and Somatic Cell Genetics of Plants: Laboratory Procedures and Their Applications. Orlando: Academic Press.
41. Stanier, R, Ingrahm, J, Wheelis, M et al., 1986. The Microbial World. New Jersey: Prentice-Hall.
42. Dhringra, O D & Sinclair, J B 1985. Basic plant pathology methods. Boca Raton, Fla.: CRC Press.
43. Maniatis, T, Fritsch, E F & Sambrook, J 1985. Molecular Cloning: A Laboratory Manual: DNA Cloning. New York: Cold Spring Harbor.
44. Gait 1984. Oligonucleotide Synthesis-A Practical Approach. Washington, D.C.: IRL Press.
45. Hames, D D & Higgins, S J 1984. Nucleic Acid Hybridization: A Practical Approach. Washington D.C.: IRL Press.
46. Watson, J D, Gilman, M, Witowski, J et al., 1992. Recombinant DNA. New York: Scientific American Books.
47. Brown, E L, Belagaje, R, Ryan, M J et al., 1979. Chemical synthesis and cloning of a tyrosine tRNA gene. Methods Enzymol, 68: 109-151.
48. Beaucage, S L & Caruthers, M H 1981. Deoxynucleoside phosphoramidites—a new class of key intermediates for deoxypolynucleotide synthesis. Tetra Letters, 22: 1859-1862.
49. Needham-VanDevanter, D R, Hurley, L H, Reynolds, V L et al., 1984. Characterization of an adduct between CC-1065 and a defined oligodeoxynucleotide duplex. Nucleic Acids Res, 12: 159-168.
50. Lee, L-Y & Gelvin, S B 2008. T-DNA binary vectors and systems. Plant Physiol, 146: 325-332.
51. Rogers, S G, Klee, H J, Horsch, R B et al., 2003. Improved vectors for plant transformation: Expression cassette vectors and new selectable markers Methods Enzymol, 153: 253-277.
52. Schardl, C L, Byrd, A D, Benzion, G et al., 1987. Design and construction of a versatile system for the expression of foreign genes in plants. Gene, 61: 1-11.
53. Nakagawa, T, Ishiguro, S & Kimura, T 2009. Gateway vectors for plant transformation. Plant Biotechnology, 26: 275-284.
54. Shahin, E A 1985. Totipotency of tomato protoplasts. Theor Appl Genet, 69: 235-240.
55. Fromm, M, Taylor, L P & V., W 1985. Expression of genes transferred into monocot and dicot plant cells by electroporation. Proc Natl Acad Sci USA, 82: 5824-5828.
56. Fromm, M E, Taylor, L P & Walbot, V 1986. Stable transformation of maize after gene transfer by electroporation. Nature, 319: 791-3.
57. Riggs, C D & Bates, G W 1986. Stable transformation of tobacco by electroporation: evidence for plasmid concatenation. Proc Natl Acad Sci USA, 83: 5602-5606.
58. D'Halluin, K, Bonne, E, Bossut, M et al., 1992. Transgenic maize plants by tissue electroporation. Plant Cell, 4: 1495-1505.
59. Laursen, C M, Krzyzek, R A, Flick, C E et al., 1994. Production of fertile transgenic maize by electroporation of suspension culture cells Plant Mol Biol, 24: 51-61
60. Crossway, A, Oakes, J V, Irvine, J M et al., 1986. Integration of foreign DNA following microinjection of tobacco mesophyll protoplasts. Mol Gen Genet, 202: 179-185.
61. Griesbach, R J 1983. Protoplast microinjection. Plant Mol Biol Report, 1: 32-37.
62. Sporlein, B & Koop, H-U 1991. Lipofectin: direct gene transfer to higher plants using cationic liposomes. Theor Appl Genet, 83: 1-5.
63. Ohgawara, T, Uchimiya, H & Harada, H 1983. Uptake of liposome-encapsulated plasmid DNA by plant protoplasts and molecular fate of foreign DNA Protoplasma, 116: 145-148.
64. Deshayes, A, Herrera-Estrella, L & Caboche, M 1985. Liposome-mediated transformation of tobacco mesophyll protoplasts by an *Escherichia coli* plasmid. EMBO (Eur Mol Biol Organ) J, 4: 2731-7.
65. Christou, P, Murphy, J E & Swain, W F 1987. Stable transformation of soybean by electroporation and root formation from transformed callus. Proc Natl Acad Sci USA, 84: 3962-3966.
66. Horsch, R B, Fry, J E, Hoffmann, N L et al., 1985. A Simple and General Method for Transferring Genes into Plants. Science, 227: 1229-1231.
67. Paszkowski, J, Shillito, R D, Saul, M et al., 1984. Direct gene transfer to plants. Embo J, 3: 2717-2722.
68. Hooykaas-Van Slogteren, G M, Hooykaas, P J & Schilperoort, R A 1984. Expression of Ti plasmid genes in monocotyledonous plants infected with *Agrobacterium Tumefaciens*. Nature, 311: 763-764.

69. Rogers, S G, Horsch, R. B., and Fraley, R. T. 1986. Gene transfer in plants: Production of transformed plants using Ti-plasmid vectors. 1986. Gene transfer in plants: Production of transformed plants using Ti-plasmid vectors. Methods Enzymol, 118: 627-640.
70. Bevan, M W & Chilton, M-D 1982. T-DNA of the *Agrobacterium* Ti and Ri plasmids. Annu Rev Genet, 16: 357-384.
71. Klein, T M, Fromm, M, Weissinger, A et al., 1988. Transfer of foreign genes into intact maize cells with high-velocity microprojectiles. Proc Natl Acad Sci USA, 85: 4305-4309.
72. Klein, T M, Gradziel, T, Fromm, M E et al., 1988. Factors influencing gene delivery into *Zea mays* cells by high-velocity microprojectiles. Biotechnology, 6: 559-563.
73. McCabe, D E, Swain, W F, Martinell, B J et al., 1988. Stable transformation of soybean (*Glycine max*) by particle acceleration. Biotechnology, 6: 923-926.
74. Sanford, J C, Smith, F D & Rushell, J A 1993. Optimizing the biolistic process for different biological application. In Wu R, editor. The Methods in Enzymology 483-509. Orlando: Academic Press.
75. Freeman, J P, Draper, J, Davey, M R et al., 1984. A Comparison of Methods for Plasmid Delivery into Plant Protoplasts. Plant Cell Physiol, 25: 1353-1365.
76. Frame, B R, Drayton, P R, Bagnall, S V et al., 1994. Production of fertile transgenic maize plants by silicon carbide whisker-mediated transformation. Plant J, 6: 941-948.
77. Thompson, J A, Drayton, P, Frame, B et al., 1995. Maize transformation utilizing silicon carbide whiskers: a review. Euphytica, 85: 75-80.
78. Guo, Y, Liang, H & Berns, M W 1995. Laser-mediated gene transfer in rice. Physiol Plant, 93: 19-24.
79. Bach, Y A, Kereim, M A, Yehia, M A et al., 2005. Production of fertile transgenic wheat plants by laser micropuncture. Photochem Photobiol Sci, 4: 803-807.
80. Bao, S, Thrall, B D & Miller, D L 1997. Transfection of a reporter plasmid into cultured cells by sonoporation in vitro. Ultrasound in Medicine and Biology, 23: 953-959.
81. Finer, K R & Finer, J J 2000. Use of *Agrobacterium* expressing green fluorescent protein to evaluate colonization of sonication-assisted *Agrobacterium*-mediated transformation-treated soybean cotyledons. Lett Appl Microbiol, 30: 406-10.
82. Amoah, B K, Wu, H, Sparks, C et al., 2001. Factors influencing *Agrobacterium*-mediated transient expression of uidA in wheat inflorescence tissue. J Exp Bot, 52: 1135-42.
83. Krens, F A, Molendijk, L, Wullems, G J et al., 1982. In Vitro transformation of plant protoplasts with Ti-plasmid DNA. Nature, 296: 72-74.
84. Bechtold, N & Pelletier, G 1998. In planta *Agrobacterium*-mediated transformation of adult *Arabidopsis thaliana* plants by vacuum infiltration. Methods Mol Biol, 82: 259-66.
85. Clough, S J & Bent, A F 1998. Floral dip: a simplified method for *Agrobacterium*-mediated transformation of *Arabidopsis thaliana*. The Plant Journal, 16: 735-743.
86. Broothaerts, W, Mitchell, H J, Weir, B et al., 2005. Gene transfer to plants by diverse species of bacteria. Nature, 433: 629-633.
87. Meinkoth, J & Wahl, G 1984. Hybridization of nucleic acids immobilized on solid supports. Anal Biochem, 138: 267-284.
88. Tijssen, P 1993. Overview of principles of hybridization and the strategy of nucleic acid probe assays. Laboratory Techniques in Biochemistry and Molecular Biology—Hybridization with Nucleic Acid Probes: Part I. New York: Elsevier.
89. Ausubel, F M, Brent, R, Kingston, R E et al., 1995. Current Protocols in Molecular Biology. New York: Greene Publishing and Wiley-Interscience.
90. Smith, T F & Waterman, M S 1981. Comparison of biosequences. Adv Appl Math, 2: 482-489.
91. Needleman, S B & Wunsch, C D 1970. A general method applicable to the search for similarities in the amino acid sequence of two proteins. J Mol Biol, 48: 443-453.
92. Pearson, W R & Lipman, D J 1988. Improved tools for biological sequence comparison. Proc Natl Acad Sci USA, 85: 2444-2448.
93. Higgins, D G & Sharp, P M 1989. Fast and sensitive multiple sequence alignments on a microcomputer. Comput Appl Biosci, 5: 151-153.
94. Higgins, D G & Sharp, P M 1988. CLUSTAL: a package for performing multiple sequence alignment on a microcomputer. Gene, 73: 237-244.
95. Higgins, D G, Bleasby, A J & Fuchs, R 1992. CLUSTAL V: improved software for multiple sequence alignment. Comput Appl Biosci, 8: 189-191.
96. Feng, D F & Doolittle, R F 1987. Progressive sequence alignment as a prerequisite to correct phylogenetic trees. J Mol Evol, 25: 351-360.
97. Henikoff, S & Henikoff, J 1989. Amino acid substitution matrices from protein blocks Proc Natl Acad Sci USA, 89: 10915-10919.
98. Li, et al., 2006. "Oil content of *Arabidopsis* seeds: The influence of seed anatomy, light and plant-to-plant variation." Phytochemistry, 67: 904-915.
99. Joshi, et al., 1997. "Context sequences of translation codons in plants." Plant Mol Biol 35:993-1001.

What is claimed is:

1. A nucleic acid construct comprising a nucleic acid having promoter activity in a plant operably linked to a heterologous DNA of interest, wherein the nucleic acid having promoter activity in a plant is selected from the group consisting of:
   (a) a nucleic acid comprising nucleotides 1-1769 of SEQ ID NO:8;
   (b) a nucleic acid comprising nucleotides 1-863 of SEQ ID NO:10; and
   (c) a nucleic acid comprising nucleotides 1-442 of SEQ ID NO:11.

2. The isolated nucleic acid construct of claim 1, further comprising a nucleic acid having terminator activity in a plant operably linked to the DNA of interest, wherein the nucleic acid having terminator activity in a plant is
   a nucleic acid comprising nucleotides 1-659 of SEQ ID NO:9.

3. The nucleic acid construct of claim 1, wherein the DNA of interest encodes a peptide, polypeptide or protein.

4. The nucleic acid construct of claim 1, wherein the DNA of interest encodes a functional RNA, an antisense RNA or a sense RNA.

5. A vector comprising the nucleic acid construct of claim 1.

6. A plant cell having stably incorporated into its genome the nucleic acid construct of claim 1.

7. The plant cell of claim 6, wherein the plant cell is derived from a plant selected from the group consisting of acacia, alfalfa, aneth, apple, apricot, artichoke, arugula, asparagus, avocado, banana, barley, beans, beech, beet, Bermuda grass, blackberry, blueberry, Blue grass, broccoli, brussel sprouts, cabbage, camelina, canola, cantaloupe, carrot, cassava, cauliflower, celery, cherry, chicory, cilantro, citrus, clementines, coffee, com, cotton, cucumber, duckweed, Douglas fir, eggplant, endive, escarole, eucalyptus, fennel, fescue, figs, forest trees, garlic, gourd, grape, grapefruit, honey dew, jatropha, jicama, kiwifruit, lettuce, leeks, lemon, lime, Loblolly pine, maize, mango, melon, mushroom, nectarine, nut, oat, okra, onion, orange, an ornamental plant, palm, papaya, parsley, pea, peach, peanut, pear, pepper, persimmon, pine, pineapple, plantain, plum, pomegranate, poplar, potato, pumpkin, quince, radiata pine, radicchio, radish, rapeseed, raspberry, rice, rye, rye grass, scallion, sorghum, Southern pine, soybean, spinach, squash, strawberry, sugarbeet, sugarcane, sunflower, sweet potato, sweetgum, switchgrass, tangerine, tea, tobacco, tomato, turf, turnip, a vine, watermelon, wheat, yams, and zucchini.

8. A plant having stably incorporated into its genome the nucleic acid construct of claim 1.

9. The plant of claim 8, wherein the plant is selected from the group consisting of acacia, alfalfa, aneth, apple, apricot, artichoke, arugula, asparagus, avocado, banana, barley, beans, beech, beet, Bermuda grass, blackberry, blueberry, Blue grass, broccoli, brussel sprouts, cabbage, camelina, canola, cantaloupe, carrot, cassava, cauliflower, celery, cherry, chicory, cilantro, citrus, clementines, coffee, corn, cotton, cucumber, duckweed, Douglas fir, eggplant, endive, escarole, eucalyptus, fennel, fescue, figs, forest trees, garlic, gourd, grape, grapefruit, honey dew, jatropha, jicama, kiwifruit, lettuce, leeks, lemon, lime, Loblolly pine, maize, mango, melon, mushroom, nectarine, nut, oat, okra, onion, orange, an ornamental plant, palm, papaya, parsley, pea, peach, peanut, pear, pepper, persimmon, pine, pineapple, plantain, plum, pomegranate, poplar, potato, pumpkin, quince, radiata pine, radicchio, radish, rapeseed, raspberry, rice, rye, rye grass, scallion, sorghum, Southern pine, soybean, spinach, squash, strawberry, sugarbeet, sugarcane, sunflower, sweet potato, sweetgum, switchgrass, tangerine, tea, tobacco, tomato, turf, turnip, a vine, watermelon, wheat, yams, and zucchini.

10. A transgenic seed of the plant of claim 8, wherein the seed comprises the nucleic acid construct.

11. A method for expressing a DNA of interest in a plant cell, the method comprising: a) transforming a plant cell with the nucleic acid construct of claim 1 and b) growing the plant cell to express the DNA of interest.

12. The method of claim 11 further comprising regenerating a stably transformed plant from the plant cell, wherein expression of the DNA of interest alters a phenotype of the plant.

13. The method of claim 11, wherein the plant cell is derived from a plant selected from the group consisting of acacia, alfalfa, aneth, apple, apricot, artichoke, arugula, asparagus, avocado, banana, barley, beans, beech, beet, Bermuda grass, blackberry, blueberry, Blue grass, broccoli, brussel sprouts, cabbage, camelina, canola, cantaloupe, carrot, cassava, cauliflower, celery, cherry, chicory, cilantro, citrus, clementines, coffee, com, cotton, cucumber, duckweed, Douglas fir, eggplant, endive, escarole, eucalyptus, fennel, fescue, figs, forest trees, garlic, gourd, grape, grapefruit, honey dew, jatropha, jicama, kiwifruit, lettuce, leeks, lemon, lime, Loblolly pine, maize, mango, melon, mushroom, nectarine, nut, oat, okra, onion, orange, an ornamental plant, palm, papaya, parsley, pea, peach, peanut, pear, pepper, persimmon, pine, pineapple, plantain, plum, pomegranate, poplar, potato, pumpkin, quince, radiata pine, radicchio, radish, rapeseed, raspberry, rice, rye, rye grass, scallion, sorghum, Southern pine, soybean, spinach, squash, strawberry, sugarbeet, sugarcane, sunflower, sweet potato, sweetgum, switchgrass, tangerine, tea, tobacco, tomato, turf, turnip, a vine, watermelon, wheat, yams, and zucchini.

14. The nucleic acid construct of claim 2, wherein the DNA of interest encodes a peptide, polypeptide or protein.

15. The nucleic acid construct of claim 2, wherein the DNA of interest encodes a functional RNA, an antisense RNA or a sense RNA.

16. A vector comprising the nucleic acid construct of claim 2.

17. A plant cell having stably incorporated into its genome the nucleic acid construct of claim 2.

18. The plant cell of claim 17, wherein the plant cell is derived from a plant selected from the group consisting of acacia, alfalfa, aneth, apple, apricot, artichoke, arugula, asparagus, avocado, banana, barley, beans, beech, beet, Bermuda grass, blackberry, blueberry, Blue grass, broccoli, brussel sprouts, cabbage, camelina, canola, cantaloupe, carrot, cassava, cauliflower, celery, cherry, chicory, cilantro, citrus, clementines, coffee, com, cotton, cucumber, duckweed, Douglas fir, eggplant, endive, escarole, eucalyptus, fennel, fescue, figs, forest trees, garlic, gourd, grape, grapefruit, honey dew, jatropha, jicama, kiwifruit, lettuce, leeks, lemon, lime, Loblolly pine, maize, mango, melon, mushroom, nectarine, nut, oat, okra, onion, orange, an ornamental plant, palm, papaya, parsley, pea, peach, peanut, pear, pepper, persimmon, pine, pineapple, plantain, plum, pomegranate, poplar, potato, pumpkin, quince, radiata pine, radicchio, radish, rapeseed, raspberry, rice, rye, rye grass, scallion, sorghum, Southern pine, soybean, spinach, squash, strawberry, sugarbeet, sugarcane, sunflower, sweet potato, sweetgum, switchgrass, tangerine, tea, tobacco, tomato, turf, turnip, a vine, watermelon, wheat, yams, and zucchini.

19. A plant having stably incorporated into its genome the nucleic acid construct of claim 2.

20. The plant of claim 19, wherein the plant is selected from the group consisting of acacia, alfalfa, aneth, apple, apricot, artichoke, arugula, asparagus, avocado, banana, barley, beans, beech, beet, Bermuda grass, blackberry, blueberry, Blue grass, broccoli, brussel sprouts, cabbage, camelina, canola, cantaloupe, carrot, cassava, cauliflower, celery, cherry, chicory, cilantro, citrus, clementines, coffee, corn, cotton, cucumber, duckweed, Douglas fir, eggplant, endive, escarole, eucalyptus, fennel, fescue, figs, forest trees, garlic, gourd, grape, grapefruit, honey dew, jatropha, jicama, kiwifruit, lettuce, leeks, lemon, lime, Loblolly pine, maize, mango, melon, mushroom, nectarine, nut, oat, okra, onion, orange, an ornamental plant, palm, papaya, parsley, pea, peach, peanut, pear, pepper, persimmon, pine, pineapple, plantain, plum, pomegranate, poplar, potato, pumpkin, quince, radiata pine, radicchio, radish, rapeseed, raspberry, rice, rye, rye grass, scallion, sorghum, Southern pine, soybean, spinach, squash, strawberry, sugarbeet, sugarcane, sunflower, sweet potato, sweetgum, switchgrass, tangerine, tea, tobacco, tomato, turf, turnip, a vine, watermelon, wheat, yams, and zucchini.

21. A transgenic seed of the plant of claim 19, wherein the seed comprises the nucleic acid construct.

22. A method for expressing a DNA of interest in a plant cell, the method comprising: a) transforming a plant cell with the nucleic acid construct of claim 2 and b) growing the plant cell to express the DNA of interest.

23. The method of claim 22 further comprising regenerating a stably transformed plant from the plant cell, wherein expression of the DNA of interest alters a phenotype of the plant.

24. The method of claim 12, wherein the plant cell is derived from a plant selected from the group consisting of acacia, alfalfa, aneth, apple, apricot, artichoke, arugula, asparagus, avocado, banana, barley, beans, beech, beet, Bermuda grass, blackberry, blueberry, Blue grass, broccoli, brussel sprouts, cabbage, camelina, canola, cantaloupe, carrot, cassava, cauliflower, celery, cherry, chicory, cilantro, citrus, clementines, coffee, corn, cotton, cucumber, duckweed, Douglas fir, eggplant, endive, escarole, eucalyptus, fennel, fescue, figs, forest trees, garlic, gourd, grape, grapefruit, honey dew, jatropha, jicama, kiwifruit, lettuce, leeks, lemon, lime, Loblolly pine, maize, mango, melon, mushroom, nectarine, nut, oat, okra, onion, orange, an ornamental plant, palm, papaya, parsley, pea, peach, peanut, pear, pepper, persimmon, pine, pineapple, plantain, plum, pomegranate, poplar, potato, pumpkin, quince, radiata pine, radicchio, radish, rapeseed, raspberry, rice, rye, rye grass, scallion, sorghum, Southern pine, soybean, spinach, squash, strawberry, sugarbeet, sugarcane, sunflower, sweet potato, sweetgum, switchgrass, tangerine, tea, tobacco, tomato, turf, turnip, a vine, watermelon, wheat, yams, and zucchini.

25. The method of claim 22, wherein the plant cell is derived from a plant selected from the group consisting of acacia, alfalfa, aneth, apple, apricot, artichoke, arugula, asparagus, avocado, banana, barley, beans, beech, beet, Bermuda grass, blackberry, blueberry, Blue grass, broccoli, brussel sprouts, cabbage, camelina, canola, cantaloupe, carrot, cassava, cauliflower, celery, cherry, chicory, cilantro, citrus, clementines, coffee, corn, cotton, cucumber, duckweed, Douglas fir, eggplant, endive, escarole, eucalyptus, fennel, fescue, figs, forest trees, garlic, gourd, grape, grapefruit, honey dew, jatropha, jicama, kiwifruit, lettuce, leeks, lemon, lime, Loblolly pine, maize, mango, melon, mushroom, nectarine, nut, oat, okra, onion, orange, an ornamental plant, palm, papaya, parsley, pea, peach, peanut, pear, pepper, persimmon, pine, pineapple, plantain, plum, pomegranate, poplar, potato, pumpkin, quince, radiata pine, radicchio, radish, rapeseed, raspberry, rice, rye, rye grass, scallion, sorghum, Southern pine, soybean, spinach, squash, strawberry, sugarbeet, sugarcane, sunflower, sweet potato, sweetgum, switchgrass, tangerine, tea, tobacco, tomato, turf, turnip, a vine, watermelon, wheat, yams, and zucchini.

26. The method of claim 23, wherein the plant cell is derived from a plant selected from the group consisting of acacia, alfalfa, aneth, apple, apricot, artichoke, arugula, asparagus, avocado, banana, barley, beans, beech, beet, Bermuda grass, blackberry, blueberry, Blue grass, broccoli, brussel sprouts, cabbage, camelina, canola, cantaloupe, carrot, cassava, cauliflower, celery, cherry, chicory, cilantro, citrus, clementines, coffee, com, cotton, cucumber, duckweed, Douglas fir, eggplant, endive, escarole, eucalyptus, fennel, fescue, figs, forest trees, garlic, gourd, grape, grapefruit, honey dew, jatropha, jicama, kiwifruit, lettuce, leeks, lemon, lime, Loblolly pine, maize, mango, melon, mushroom, nectarine, nut, oat, okra, onion, orange, an ornamental plant, palm, papaya, parsley, pea, peach, peanut, pear, pepper, persimmon, pine, pineapple, plantain, plum, pomegranate, poplar, potato, pumpkin, quince, radiata pine, radicchio, radish, rapeseed, raspberry, rice, rye, rye grass, scallion, sorghum, Southern pine, soybean, spinach, squash, strawberry, sugarbeet, sugarcane, sunflower, sweet potato, sweetgum, switchgrass, tangerine, tea, tobacco, tomato, turf, turnip, a vine, watermelon, wheat, yams, and zucchini.

* * * * *

SEQUENCE LISTING

```
<160> NUMBER OF SEQ ID NOS: 11

<210> SEQ ID NO 1
<211> LENGTH: 1493
<212> TYPE: DNA
<213> ORGANISM: Oryza sativa

<400> SEQUENCE: 1
gaattccaaa gagggaaata taaaaagcag agagagtata gatccaatgg tgtgggggca      60
cgcaaagaca aaatcatgca tgatctgttt agtgccgagc aaaaggcaca gtttaatcca     120
```

```
aaactgatgc taattaacta tatatgcttt catgcactaa ctgttacatc ctctgattct    180
gaaagagatg ggtggaagat tgcaaagatc aggggggagaa gatccacata aatgtgttcc    240
aaacacatgt cacatatata tgtacttaat tacttgtgtc ccatccttaa tgactagtta    300
cattatagta catatactga cagaagcata taacagtt gatccaattt taatatctgt    360
ttataggaat cctttacgcc agacctaaga acttctttgg attaaggcat ttcaacaaaa    420
ttattttatg tgtaaaaaga attggaaaga ctatgtaatg atccaaaaaa cggtgcaatg    480
tccggtactg cttcacgtac tatgggcctg ttcagcaggc cgactgcgac ggttgcgact    540
gcgcacagtg agtgtggcgc tgttcgtgcc ggctgcggca gcctcggcag ccaaacaagc    600
cctatgagta aattatatct agatatgtgt tagttactct atttgcacct actatcatga    660
taactattga agtttcgaaa ccgtaccttc tcataatttt tttacatttt tttttttgcaa    720 caaccagtat tttacatagc gattctaatt atccatctaa tttattttat aacgttataa    780
aatttataaa aatttatatg ctatataatt agctagtaat acatatatgt agccctatat    840
atactaacca tgttgtcgaa aggatattat atgagcacac actactcaat taaaaccaaa    900
agagagcccc tctcatcttt tggcaaatta aggaggggt tgaaggcatg gagttggggt    960
cggccttggt ggcttttcc cggccaggat agagaatatc cccttgggc tttgtagcag   1020 aagactccta gctagctagc tagctagcta gagagagaaa caaagaaaga gaaagtttgt   1080
gtcacacaca gacaaaaaaa aaggaagaag cagcaaagcc atcaccccaa gcaaagagg   1140 agagagtgag agagaaaccc atctagagag agagagagac taaagagcat atgagcacaa   1200
gctagagcta caagtgtgat caagccatag atagagagag agagagagga agagcgagcg   1260 aacccctattc cttgttcttg aatctgtcgt ctccaatcgg gcaggatcaa ggatcgacga   1320
ggtagagaga gttattatta ttatagagag agagaattaa ttcgagagag atctagagag   1380
agaagaagaa gagaggagat catagaagaa tgttccctgg ctcgaagaag ggcggcggcg   1440
gcggcgccgc ggtgagctcg ggtgacggcg gcggcggcag ggcggcggcg gcg          1493
```

<210> SEQ ID NO 2
<211> LENGTH: 925
<212> TYPE: DNA
<213> ORGANISM: Oryza sativa

<400> SEQUENCE: 2

```
tcacaattag ttaattaatt aatgagttaa ttaactaatt aaaccagtta atcacagcag     60
aggaaattaa ttaaattggc tcgtgctcga tcgatcgaac tgtggctaaa taagttttac    120
agctcgagtt catgcatgga ttaatggata tataattggt agcaacaggg ggtaaattat    180
tattaatgcg gcattaatca ggatgatctt gtggtattgt ggtgcatcga tcatatatat    240
gcttgatgat gatgcccaaa tgctaattaa gattatctat tttgaggatg catgtaatat    300
gttctgtgta attgtgtgtt gtgttaatta tcaagatcat gggtgtaaat gtgtaactta    360
tatttggcat tcttgcatgc taaagaaaca agctttcatt gatatatctg aggctgcatg    420
cgcgtatgtc ggtcgatcaa aaaacacaat gttaatggaa cttaaattcc aggttgatac    480
gtgtatttaa tttactgatt atggaaatat gttgagattt atttctgaaa tatgaaaaac    540
taaatgcacc tagtcgtcta tagactatag cttcggctca aggttcattc atgcgatcat    600
atgatcgaat atatatatgc acatatatgt atgtgttcat caaataaatt aaccatttat    660
gcatagttca ctagctagat gtgtgtatat acattgatga ttgatcaata tttgttctag    720
ctctgtaaaa cgttgccgca tcaattaatc tgcaatatat atataatatg ccacaagatg    780
```

-continued

| | |
|---|---|
| gatatataca tttccaaga taactatatt aattaatgag cacacacata tggcatccat | 840 |
| ctctcaatta ataagctgta ttactaataa atataataca gaaaatttgt gctacatata | 900 |
| tatcctccca tatatggaat tttga | 925 |

<210> SEQ ID NO 3
<211> LENGTH: 641
<212> TYPE: DNA
<213> ORGANISM: Oryza sativa

<400> SEQUENCE: 3

| | |
|---|---|
| ttgtcgaaag gatattatat gagcacacac tactcaatta aaaccaaaag agagcccctc | 60 |
| tcatcttttg gcaaattaaa ggaggggttg aaggcatgga gttggggtcg gccttggtgg | 120 |
| cttttcccg gccaggatag agaatatcac ccttgggctt tgtagcagaa gactcctagc | 180 |
| tagctagcta gctagctaga gagagaaaca agaaagaga agtttgtgt cacacacaga | 240 |
| caaaaaaaa ggaagaagca gcaaagccat caccccaagc aaaagaggag agagtgagag | 300 |
| agaaacccat ctagagagag agagagacta agagcatat gagcacaagc tagagctaca | 360 |
| agtgtgatca agccatagat agagagagag agagaggaag agcgagcgaa ccctattcct | 420 |
| tgttcttgaa tctgtcgtct ccaatcgggc aggatcaagg atcgacgagg tagagagagt | 480 |
| tattattatt atagagagag agaattaatt cgagagagat ctagagagag aagaagaaga | 540 |
| gaggagatca tagaagaatg ttccctggct cgaagaaggg cggcggcggc ggcgccgcgg | 600 |
| tgagctcggg tgacggcggc ggcggcaggg cggcggcggc g | 641 |

<210> SEQ ID NO 4
<211> LENGTH: 389
<212> TYPE: DNA
<213> ORGANISM: Oryza sativa

<400> SEQUENCE: 4

| | |
|---|---|
| aagaagcagc aaagccatca ccccaagcaa aagaggagag agtgagagag aaacccatct | 60 |
| agagagagag agagactaaa gagcatatga gcacaagcta gagctacaag tgtgatcaag | 120 |
| ccatagatag agagagagag agaggaagag cgagcgaacc ctattccttg ttcttgaatc | 180 |
| tgtcgtctcc aatcgggcag gatcaaggat cgacgaggta gagagagtta ttattattat | 240 |
| agagagagag aattaattcg agagagatct agagagagaa gaagaagaga ggagatcata | 300 |
| gaagaatgtt ccctggctcg aagaaggcg gcggcggcgg cgccgcggtg agctcgggtg | 360 |
| acggcggcgg cggcagggcg gcggcggcg | 389 |

<210> SEQ ID NO 5
<211> LENGTH: 1428
<212> TYPE: DNA
<213> ORGANISM: Oryza sativa

<400> SEQUENCE: 5

| | |
|---|---|
| gaattccaaa gagggaaata taaaaagcag agagagtata gatccaatgg tgtgggggca | 60 |
| cgcaaagaca aaatcatgca tgatctgttt agtgccgagc aaaaggcaca gtttaatcca | 120 |
| aaactgatgc taattaacta tatatgcttt catgcactaa ctgttacatc ctctgattct | 180 |
| gaaagagatg ggtggaagat tgcaaagatc agggggagaa gatccacata aatgtgttcc | 240 |
| aaacacatgt cacatatata tgtacttaat tacttgtgtc ccatccttaa tgactagtta | 300 |
| cattatagta catatactga cagaagcata taacagtt gatccaattt taatatctgt | 360 |

```
ttataggaat cctttacgcc agacctaaga acttctttgg attaaggcat ttcaacaaaa      420
ttattttatg tgtaaaaaga attggaaaga ctatgtaatg atccaaaaaa cggtgcaatg      480
tccggtactg cttcacgtac tatgggcctg ttcagcaggc cgactgcgac ggttgcgact      540
gcgcacagtg agtgtggcgc tgttcgtgcc ggctgcggca gcctcggcag ccaaacaagc      600
cctatgagta aattatatct agatatgtgt tagttactct atttgcacct actatcatga      660
taactattga agtttcgaaa ccgtaccttc tcataatttt tttacatttt ttttttgcaa      720
caaccagtat tttacatagc gattctaatt atccatctaa tttattttat aacgttataa      780
aatttataaa aatttatatg ctatataatt agctagtaat acatatatgt agccctatat      840
atactaacca tgttgtcgaa aggatattat atgagcacac actactcaat aaaaccaaa       900 agagagcccc tctcatcttt tggcaaatta aggagggggt tgaaggcatg gagttggggt      960
cggccttggt ggcttttttcc cggccaggat agagaatatc acccttgggc tttgtagcag     1020
aagactccta gctagctagc tagctagcta gagagagaaa caagaaagaa gaaagtttgt     1080
gtcacacaca gacaaaaaaa aaggaagaag cagcaaagcc atcaccccaa gcaaaagagg     1140
agagagtgag agagaaaccc atctagagag agagagagac taaagagcat atgagcacaa     1200
gctagagcta caagtgtgat caagccatag atagagagag agagagagga agagcgagcg     1260
aaccctattc cttgttcttg aatctgtcgt ctccaatcgg gcaggatcaa ggatcgacga     1320
ggtagagaga gttattatta ttatagagag agagaattaa ttcgagagag atctagagag     1380
agaagaagaa gagaggagat catagaagaa tgttccctgg ctcgaaga                  1428

<210> SEQ ID NO 6
<211> LENGTH: 576
<212> TYPE: DNA
<213> ORGANISM: Oryza sativa

<400> SEQUENCE: 6
ttgtcgaaag gatattatat gagcacacac tactcaatta aaaccaaaag agagcccctc       60
tcatcttttg gcaaattaaa ggaggggttg aaggcatgga gttggggtcg ccttggtgg       120 cttttttcccg gccaggatag agaatatcac ccttgggctt tgtagcagaa gactcctagc    180
tagctagcta gctagctaga gagagaaaca agaaagaga aagtttgtgt cacacacaga      240
caaaaaaaaa ggaagaagca gcaaagccat caccccaagc aaaagaggag agagtgagag    300
agaaacccat ctagagagag agagagacta aagagcatat gagcacaagc tagagctaca    360
agtgtgatca agccatagat agagagagag agaggaagag cgagcgaac cctattcct      420 tgttcttgaa tctgtcgtct ccaatcgggc aggatcaagg atcgacgagg tagagagagt    480
tattattatt atagagagag agaattaatt cgagagagat ctagagagag aagaagaaga    540
gaggagatca tagaagaatg ttccctggct cgaaga                              576

<210> SEQ ID NO 7
<211> LENGTH: 324
<212> TYPE: DNA
<213> ORGANISM: Oryza sativa

<400> SEQUENCE: 7
aagaagcagc aaagccatca ccccaagcaa aagaggagag agtgagagag aaacccatct       60
agagagagag agagactaaa gagcatatga gcacaagcta gagctacaag tgtgatcaag     120
ccatagatag agagagagag aggaagagag cgagcgaacc ctattccttg ttcttgaatc     180
tgtcgtctcc aatcgggcag gatcaaggat cgacgaggta gagagagtta ttattattat     240
```
agagagagag aattaattcg agagagatct agagagagaa gaagaagaga ggagatcata      300
gaagaatgtt ccctggctcg aaga                                             324

<210> SEQ ID NO 8
<211> LENGTH: 1769
<212> TYPE: DNA
<213> ORGANISM: Brassica rapa

<400> SEQUENCE: 8
cagtaacact ctctttacac attgatgcat aattctccac atatcactaa accatgttta       60
tgcataactc aaagttttgc tgccatattc ttatgttatt ttctcgcttt aaattccaga      120
ttatattcct tcactaaatg ctacattgaa catttccctg ttcatattta atgcaaaaaa      180
ttatagtata tatttaaaat ttctgcagat ttaatgtagt tttatactcc tagatcatat      240
gctctctttt ttttgtgtgc atatcatttt cttaagtatg catatcaatc ccaacgccat      300
attcgttgga ttattcttgt tctacgtaaa tataccatat gggacctccc actcatacat      360
atcaggttga ccatctcatg tatatgaata tattcattta ccaaaatcaa attattatga      420
actatgcgat tgatcattga tgttggaaaa taaaagaat tatgcgatag atggacttgc       480
tatgcgatga gtgtaattga ttttttttgag gtaagacaat tcatcatcat ttgtataaag     540
aatagtttag ttgatgtagt tcacgtttgt aaaccatatt ttctattttg gtcaatcaac      600
gttttcgtta taaaaataaa ttccacctga gggtttgtat ttggtaataa tatacggtca      660
cttagtttat aacgaactca tcattgctta gaattgtata ttcagctcat aattaaccaa      720
aaaaggttta accattaatg ataaaacccc ttgtcgaatt ttttgtttag atatgtgtgt      780
atgtgtcctg attgcaatat ataacgatgt agaaatacta taactataag tctagtatac      840
gactatcctc gtgcgatcat tgaatagaat atatacatat ataactttaa tatattaaac      900
tttaaaaagt aaagtttata atctcgtttt tttattattc ttctcgaatt tatttttaat      960
ttattacaca tattaataag tacttatata catccaaatt aatcaagcag aaaaaacaaa     1020
ttaaaggata ataataaaaa tggttttaaa acgtgctcat tgtttgaatg ttagtagaga     1080
gaaataacaa aaaaaatata ctactccagt agattagcac tacatcaaat tcgagatatt     1140
tttagatgca ttaatgctta tatttatggc agaaagtgaa aaatgctagt gttttttgtaa    1200 aatttaatgc atacatatta caaacgcctt ccatctaata taacatcttt tatgtatagc     1260
taacttgtat aggatctccg atgttaaaac tcaccttttt caacaacaaa aaagaaatca     1320
aaattaattt attttttggta attacaaatt tgcaacattt taaagtcatt tgagaaatac    1380
atgaattatt tcatgtatac gtatattcct ttacagacat tttatactga aagtaattca    1440
aaggtattca agctagcgac agtatctttt cgcaaaggaa cgtctgtgta ctagtctaaa    1500
actttagttc tcttccttgc ttagtaatga taaaacaata gtattaatta ctataatatt    1560
ataaccattt tctttttcaa aaaaatatta ataaaaaat tattcacaag aaaaataaaa    1620
agaagacgag agagagagaa ggagaaagag caaaaagccg tcatctgatc tcttcaaaac    1680
cgcatcgtat tctctcacat ttttgcatca cattcgtttc cttgaatccc tctgttagag    1740
agagagagaa agaaagtcat agagagaga                                      1769

<210> SEQ ID NO 9
<211> LENGTH: 659
<212> TYPE: DNA
<213> ORGANISM: Brassica rapa

<400> SEQUENCE: 9

```
taaaattgtt tatttaaga tgtgatgtat gagaacgtga gaaggagata tatattttgt      60
tttatgagct tgacttaggt ttagagatga ggcataaaaa aatacaaact tgttatgtt     120
tatcggatta gttttgctcg tgtctttaat ttgtactgaa attatgtatc attattgttg    180
ctataatatc taggttctat tatgtactta ttcattattc tccagccaac tgtttgaaaa    240
ttgatgatta cagtgctagt cagtagaatg gccaagtgat tatatgatta tgttttcttt    300
gcttttaatc aaccactaat tattttcatt ttttgtatgt ttatgctgaa ctattttaat    360
ataaatattt gatagcagat taccttttgt tattttaatt aataactgaa ataaataaa     420
ccctcaattt attttataag ttttttacga ctttttaac taacagtctt accaatcaga    480
tattcagatg catatacaaa atgtaaaatc tatactaa agtatagagg tttaaccaat     540
gtatatgtgt atcacatata atatgcctta accggtatat atacgaacgt acgtagcatc    600
ttatgacaaa ttaaataatg aacatttatg ggtagagaaa atgagatcgc tcatgtttc     659
```

<210> SEQ ID NO 10
<211> LENGTH: 863
<212> TYPE: DNA
<213> ORGANISM: Brassica rapa

<400> SEQUENCE: 10

```
aagtaaagtt tataatctcg ttttttatt attcttctcg aatttatttt taatttatta      60
cacatattaa taagtactta tatacatcca aattaatcaa gcagaaaaaa caaattaaag    120
gataataata aaaatggttt taaaacgtgc tcattgtttg aatgttagta gagagaaata    180
acaaaaaaaa tatactactc cagtagatta gcactacatc aaattcgaga tattttaga    240
tgcattaatg cttatattta tggcagaaag tgaaaaatgc tagtgttttt gtaaaattta    300
atgcatacat attacaaacg ccttccatct aatataacat cttttatgta tagctaactt    360
gtataggatc tccgatgtta aaactcacct ttttcaacaa caaaaaagaa atcaaaatta    420
attttatttt ggtaattaca aatttgcaac attttaaagt catttgagaa atacatgaat    480
tatttcatgt atacgtatat tcctttacag acatttata ctgaaagtaa ttcaaggta     540
ttcaagctag cgacagtatc ttttcgcaaa ggaacgtctg tgtactagtc taaaacttta    600
gttctcttcc ttgcttagta atgataaaac aatagtatta attactataa tattataacc    660
attttctttt tcaaaaaaat attaataaaa aaattattca caagaaaaat aaaagaaga     720
cgagagagag agaaggagaa agagcaaaaa gccgtcatct gatctcttca aaaccgcatc    780
gtattctctc acatttttgc atcacattcg tttccttgaa tccctctgtt agagagagag    840
agaaagaaag tcatagagag aga                                            863
```

<210> SEQ ID NO 11
<211> LENGTH: 442
<212> TYPE: DNA
<213> ORGANISM: Brassica rapa

<400> SEQUENCE: 11

```
tttattttg gtaattacaa atttgcaaca ttttaaagtc atttgagaaa tacatgaatt      60
atttcatgta tacgtatatt cctttacaga cattttatac tgaaagtaat tcaaggtat    120
tcaagctagc gacagtatct tttcgcaaag gaacgtctgt gtactagtct aaaactttag    180
ttctcttcct tgcttagtaa tgataaaaca atagtattaa ttactataat attataacca    240
ttttcttttt caaaaaaata ttaataaaaa aattattcac aagaaaaata aaagaagac     300
```

```
gagagagaga gaaggagaaa gagcaaaaag ccgtcatctg atctcttcaa aaccgcatcg    360
tattctctca catttttgca tcacattcgt ttccttgaat ccctctgtta gagagagaga    420
gaaagaaagt catagagaga ga                                             442
```